US011364330B2

(12) United States Patent
Zarate

(10) Patent No.: US 11,364,330 B2
(45) Date of Patent: Jun. 21, 2022

(54) SYSTEM AND METHOD FOR FACILITATING EXTRACORPOREAL INACTIVATION OF PATHOGENS OF BLOOD PRODUCTS

(71) Applicant: Alfredo R. Zarate, Bethesda, MD (US)

(72) Inventor: Alfredo R. Zarate, Bethesda, MD (US)

( * ) Notice: Subject to any disclaimer, the term of this patent is extended or adjusted under 35 U.S.C. 154(b) by 0 days.

(21) Appl. No.: 17/470,371

(22) Filed: Sep. 9, 2021

(65) Prior Publication Data

US 2022/0143287 A1    May 12, 2022

Related U.S. Application Data

(60) Provisional application No. 63/111,867, filed on Nov. 10, 2020.

(51) Int. Cl.
*A61M 1/34* (2006.01)
*A61M 1/36* (2006.01)

(52) U.S. Cl.
CPC ........ *A61M 1/3496* (2013.01); *A61M 1/3472* (2013.01); *A61M 1/369* (2013.01); *A61M 2205/3368* (2013.01); *A61M 2205/3592* (2013.01); *A61M 2205/3606* (2013.01)

(58) Field of Classification Search
CPC .. A61M 1/3496; A61M 1/3472; A61M 1/369; A61M 2205/3368; A61M 2205/3592; A61M 2205/3606
See application file for complete search history.

(56) References Cited

U.S. PATENT DOCUMENTS 4,737,140 A * 4/1988 Lee ...................... A61M 1/3681
128/DIG. 3
6,653,293 B1    11/2003 Miwa
(Continued)

FOREIGN PATENT DOCUMENTS

| EP | 1603609 B1 | 5/2011 |
| EP | 1047458 B1 | 6/2011 |
| WO | WO2013106443 A1 | 7/2013 |

OTHER PUBLICATIONS

Klamroth R, Groner A, Simon TL, Pathogen inactivation and removal methods for plasma-derived clotting factor concentrates. Transfusion May 2014:54(5): 1406-1417.
(Continued)

*Primary Examiner* — Philip R Wiest

(57) ABSTRACT

A system and a method facilitate the extracorporeal inactivation of pathogens of blood products. The system includes an input peristaltic pump, at least one apheresis device, at least one plasma-treating system, and an output peristaltic pump. The input peristaltic pump, the apheresis device, the plasma-treating system, and the output peristaltic pump are in fluid communication with each other. The plasma-treating system includes at least one primary ultraviolet light (UVL) device, at least one heating device, and at least one cooling device. The input peristaltic pump facilitates the flow of blood from a patient through the system. The apheresis device facilitates separating of plasma from one or more blood cells. The plasma-treating system heats the plasma, inactivates pathogens within the plasma, and then cools the plasma. The output peristaltic pump facilitates the flow of blood from the system and back to the patient.

14 Claims, 15 Drawing Sheets

(56) References Cited

U.S. PATENT DOCUMENTS

| | | | |
|---|---|---|---|
| 2004/0186410 A1* | 9/2004 | Davidner | A61M 1/3683 604/5.01 |
| 2005/0059921 A1 | 3/2005 | Tu | |
| 2005/0274672 A1* | 12/2005 | Tu | A61M 1/26 210/645 |
| 2015/0283318 A1* | 10/2015 | Wang | A61B 18/20 210/638 |
| 2016/0195555 A1* | 7/2016 | Wegener | A61M 1/3693 435/3 |
| 2019/0060549 A1* | 2/2019 | Peritt | B04B 5/10 |

OTHER PUBLICATIONS

Bihm DJ, Ettinger A, Buytaert-Hoefen KA, Hendrix BK, Maldonado-Codina G, Rock G, Giclas PC, Goodrich RP. Characterization of plasma protein activity in riboflavin and UV light-treate fresh frozen plasma during 2 years of storage at -30 degrees C. Vox Sang. Feb. 2010;98(2):108-15.

Schubert P, Culibrk B, Karwal S, Serrano K, Levin E, Bu D, Bhakta V, Sheffield WP, Goodrich RP, Devine DV, Whole blood treated with riboflavin and ultraviolet light: quality assessment of all blood. Transfusion, vol. 55, Issue Apr. 4, 2015 pp. 815-823.

Blümel J, Musso D, Teitz S, Miyabayashi T, Boiler K, Schnierle BS, Baylis SA Inactivation and removal of Zika virus during manufacture of plasma-derived medicinal products. Transfusion. Mar. 2017;57(3pt2):790-796.

Stajakovic Z, Antic A, Stojanovic M, Effects of use of riboflavin and ultraviolet light for pathogen inactivation on quality of platelet concentrates Vojnosanit Pregl. Jun. 2011;68(6):489-94.

Mohr H, Gravemann U, Müller TH. Inactivation of pathogens in single units of therapeutic fresh plasma by irradiation with ultraviolet light. Transfusion. Oct. 2009;49(10):2144-51. doi: 10.1111/j.1537components produced by the buffy coat method. Transfusion. Apr. 2015;55(4):815-23.

Jimenez-Marco T, Cancino-Faure B, Girona-Llobera E, Alcover MM, Riera C, Fisa R. The Effectiveness of Riboflavin and Ultraviolet Light Pathogen Reduction Technology in Eliminating Trypanosoma Cruzi from Leukoreduced Whole Blood. Transfusion Jun. 2017;57(6):1440-1447.

Irsch J, Lin L. Pathogen inactivation of platelet and plasma blood components for transfusion using the INTERCEPT Blood System TM. Transfus Med and Hemotherapy 2011:38)1:19-31.

Marschner S, Goodrich R. Pathogen reduction technology treatment of platelets, plasma and whole blood using riboflavin and UV light. Transfus Med and Hemotherapy 2011:38(1)8-18.

Seghatchian J, Struff WG, Reichenberg S, Main properties of the THERAFLEX MB-plasma system for pathogen reduction. Transfus Med and Hemotherapy 2011:38(1):55-64.

Kim G, Karbaschi M, Cook M, Gaitas A. Light-based Methods for Whole Blood Bacterial Inactivation Enabled by a Recirculating Flow System, Photochem Photobiol. Jul. 2018;94(4):744 751.

MaClean M, Anderson JG, MacGregor SJ, White T, Atreya CD, A New Proof of Concept in Bacterial Reduction: Antimicrobial Action of Violet-Blue Light (4-5nm) in Ex Vivo Stored Plasma, J Blood Transfs 2016;2016:2920514.

Chan H-L, Gaffney PR, Waterfield MD, Anderle H, Matthiessen HP, Schwarz HP, Turecek PL, Timms JF, Proteomic analysis of UVC irradiation-induced damage of plasma proteins: Serum amyloid P component as a major target of photolysis, FEBS Letter 580 (2006) 3229-3236.

Mirshafiee H, Sharifi Z, Hosseini SM, Yare Fatemeh, Nickbakht H, Latifi H, The Effects of Ultraviolet Light and Riboflavin on Inactivation of Viruses and the Quality of Platelet Concentrates at Laboratory Scale. Avicenna J Med Biotechnol. Apr.-Jun. 2015; 7(2): 57-63.

Seltsam A, Pathogen Inactivation of Cellular Blood Products—An Additional Safety Layer in Transfusion medicine Front Med, Dec. 4, 2017, https://doi.org/10.3389/fmed.2017.00219.

Jimenez-Marco T, Ruiz-Alderon R, Bautista-Gili AM, Girona-Llober E, Role of riboflavin and UV Light Treated Plasma in Prevention of Transfusion-related Acute Lung Injury Transfus Med Hemother. Jun. 2014; 41(3): 172-175.

Hatta Y, Hershberge K, Shinya K, Proll SC, Dubielzig RR, Hatta M, Kalze MG, Kawaoka Y, Suresh M, Rimmelzwaan GF editor. Viral Replication Rate Regualtes Clinical Outcome and CD8 T Cell Rresponses during Highly Pathogenic HSN1 Influenza Virus Infection n Mice PLoS Paqthog Oct. 7, 2010.

Roizman B, Chapter 42, Multiplication, Chapter 42, Medical Microbiology, 4th edition, Baron S, Editor. Galveston (TX): University of Texas Medical Branck at Galveston.

Dhen X, Zhao B, Qu Y, Chen Y, Xiong J, Feng Y, Men D, Huang Q, Liu Y, Yang B, Ding J, Li F. Detectable serum SARS-CoV2 viral load (RNAaemia) is closely associated with drastically elevated interleukin 6 (IL-6) level in critically ill COVID-19 patients. MedRxiV, PubPeer, Mar. 10, 2020.

Kim JY, Ko JH, Kim Y, Kim YJ, Kim JM, Chung YS, Kim HM, Han MG, Kim SY, Chin BS.Viral Load Kinetics of SARS-CoV-2 Infection in First Two Patients in Korea. J Korean Med Sci. Feb. 24, 2020;35(7).

Liu Y, Yang Y, Zhang C, Huang F, Wang F, Yuan J, Wang Z, Li J, Li J, Feng C, Zhang Z, Wang L, Peng L, Chen L, Qin Y, Zhao D, Tan S, Yin L, Xu J, Zhou C, Jiang C, Liu L., Clinical and biochemical indexes from 2019-nCoV infected patients linked to viral loads and lung injury. Sci China Life Sci. Mar. 2020;63(3):364-374.

Wijeratne DT, Fernande S, Gomes L, Jeewandara C, Ginneliya A, Samarasekara S, Wijewickrama A,Hardman CS, Ogg GS, Malavige GN, Quantification of dengue virus specific T cell resposnes and correlation with viral load and clinical disease severity in acute dengue infection, PLoS Negl Trap Dis. Oct. 1, 2018;12(10):e0006540.

Singla M, Kar M, Sethi T, Kabra SK, Lodha R, Chandele A, Medigeshi GR, Immune Resposne to Dengue Virus Infection in Pediatric Patients in New Delhi, India—Association of Viremia, Inflammatory Mediators and Monocytes with Disease Severity, PLoS Negl Trap Dis. Mar. 16, 2016;10(3):e0004497.

Vaughn DW, Green S, Kalayanorooj S, Innis BL, Nimmannitya S, Suntayakorn WS, Endy TP, Raengsakulrach B, Rothman AL, Ennis FA, Nisalak A, Dengue viremia titer, antibody response pattern, and virus serotype correlate with disease severity, j Infect Dis. Jan. 2000;181(1):2-9.

Cheng HY, Huang YC, Yen TY, Hsia SH, Jsieh YC, Li CC, Chang LY, Huang LM, The correlation between the presence of viremia and clinical severity in patients with enterovirus 71 infection: a multi-center cohort study, BMC Infect Dis. Jul. 29, 2014;14:417.

Balfour HH Jr, Odumade OA, Schmeling DO, Mullan BD, Ed JA, Knight JA, Vezina HE, Thomas W, Hogquist KA,, Behavioral, virologic, and immunologic factors associated with acquisition and severity of primary Epstein-Bass virus infection in university students. J Infect Dis. Jan. 1, 2013;207(1):80-8.

McBride JM, Sheinson D, Jiang J, Lewin-Koh N, Werner BG, Chow JKL, Wu X, Tavel JA, Snydman DR, Correlation of Cytomegalovirus (CMV) Disease Severity and Mortality With CMV Viral Burden in CMV-Seropositive Donor and CMV-Seronegative Solid Organ Transplant Recipients. Open Forum Infect Dis. Jan. 14, 2019;6(2):ofz003.

Borkakoti J, Hazam RK, Mohammad A, Kumar A, Kar P.Does high viral load of hepatitis E virus influence the severity and prognosis of acute liver failure during pregnancy? J Med Virol. Apr. 2013;85(4):620-6.

Fujiwara K1, Kojima H, Yasui S, Okitsu K, Yonemitsu Y, Omata M, Yokosuka O.Hepatitis A viral load in relation to severity of the infection. J Med Virol. Feb. 2011;83(2):201-7.

Ng KT, Oong XY, Lim SH, Chook JB, Takebe Y, Chan YF, Chan KG, Hanafi NS, Pang YK, Kamarulzaman A1, Tee KK.Viral Load and Sequence Analysis Reveal the Symptom Severity, Diversity, and Transmission Clusters of Rhinovirus Infections. Clin Infect Dis. Jul. 2, 2018;67(2):261-268.

Franz A, Adams O, Willems R, Bonzel L, Neuhausen N, Schweizer-Krantz S, Ruggeberg JU, Willers R, Henrich B, Schroten H, Tenenbaum T. Correlation of viral load of respiratory pathogens and co-infections with disease severity in children hospitalized for lower respiratory tract infection. J Clin Virol. Aug. 2010;48(4):239-45.

(56) References Cited

OTHER PUBLICATIONS

Garcia-Mauriño C, Moore-Clingenpeel M, Thomas J, Mertz S, Cohen DM, Ramilo O, Mejias A. Viral Load Dynamics and Clinical Disease Severity in Infants With Respiratory Syncytial Virus Infection, a. J Infect Dis. Apr. 8, 2019;219(8):1207-1215.
Bellomo CM, Pires-Marczeski FC, Padula PJ. Viral load of patients with hantavirus pulmonary syndrome in Argentina. J Med Virol. Nov. 2015;87(11):1823-30.
Asano Y, Itakura N, Kajita Y, Suga S, Yoshikawa Tk, Yazaki T, Ozaki T, Yamanishi K, Takahashi M, Severity of viremia and clinical findings in children with varicella, J Infect Dis. Jun. 1990;161(6):1095-8.
Su CW, Huang YH, Huo TI, Shih HH, Shenn IJ, Chen SW, Lee PC, Lee SD, Wu JC, Genotypes and viremia of hepatitis B and D viruses are associated with outcomes of chronic hepatitis D patients, Gastroenterology. May 2006;130(6):1625-35.
Guss D, Sherigar J, Rosen P, Mohanty SR, Diagnosis and management of Hepatitis C infection in primary care setting, J Gen Intern Med Apr. 2018;33(4):551-557.
Mukherjee R, Burns A, Rodden D, Chang F, Chaum M, Garcia N, Bollipalli N, Niemz A, Diagnosis and management of Hep C virus infection, J Lab Autom Oct. 2015;20(5):519-38.
Agungafac G, Amin ET, Fualefac A, Takah NF, Agyingi LA, Nwobegahay J, Ondoa P, Njukeng PA, Viral load testing and the use of test results for clinical decision making for HIV treatment in Cameron: An insight into the clinic-laboratory interface, PLOSOna Jun. 11, 2018;13(6).
Van den Brand M, van den Dungen FAM, Bos MP, van Weissenbruch MM, van Furth AM, de Lange A, Rubenjan A, Peters RPH, Savelkoul PHM. Evaluation of a real-time PCR assay for detection and quantification of bacterial DNA directly in blood of preterm neonates with suspected late-onset sepsis. Crit Care. Apr. 22, 2018;22(1):105.
Yagupsky P1, Nolte FS. Quantitative aspects of septicemia. Clin Microbiol Rev. Jul. 1990;3(3):269-79.
Knott EK. Development of ultraviolet blood irradiation. Am J Surg. 1948;76:165-171.
Hancock VKK, EK Irradiated blood transfusion in the treatment of infections. Northwest Med 1934:200.
Miley G, Christensen JA. Ultraviolet blood irradiation further studies in acute infections. Am J Surg 1947 LxxIII:486-493.
Rowen RJ. Ultraviolet Blood Irradiation Therapy (Photo-Oxidation): The cure that Time Forgot. Int J Biosocial Med Research 14:115-132.
Coppard C, HannaniD, Humbert M, Gauthier V, Plumas J, Merlin E, Gabert F, Chaperot L, In vitro PUVA treatment triggers calreticulin exposition and HMGB1 release by dying T lymphocytes in GVHD: New insights in extracorporeal photopheresis. J Clin Apher. Aug. 2016;34(4):450-460.
Aubin F, Mousoon C, Ultraviolet light-induced regulatory (suppressor) T cells: an approach for promoting induction of operation allograft tolerance? Transplantation. Jan. 15, 2004;77(1 Suppl):S29-31.
Aubin F Mechanisms involved in ultraviolet light-induced immunosuppression. Eur J Dermatol. Nov.-Dec. 2003;13(6):515-23.
Loh YS, Dean MM, Johnson L, Marks DC. Treatment of platelets with riboflavin and ultraviolet light mediates complement activation and suppresses monocyte interleukin-12 production in whole blood, Vox Sang. Nov. 2015;109(4):327-35.
Marschner S, Fast LD, Baldwin WM 3rd, Slichter SJ, Goodrich RP, White blood cell inactivation after treatment with riboflavin and ultraviolet light Transfusion. 2010 No;50(11):2489-98.
Reddy HL, Doane SK, Keil SD, Marschner S, Goodrich RP, Development of a riboflavin and ultraviolet light-based device to treat whole blood, Transfusion. Jan. 2013;53 Suppl 1:131S-136STarabadkar ES, Shinohara MM, Skin Directed Therapy in Cutaneous T-Cell Lymphoma, Front Onco 2019;9:260.
Tarabadkar ES, Shinohara MM, Skin Directed Therapy in Cutaneous T-Cell Lymphoma, Front Onco treatment of steroid-refractory and steroid-dependent acute graft-versus host-disease of the skin, J Am Acad Dermatol Oct. 2011;65(4):733-738.
Feldstein JV, Bolanos-Meade J, Anders VL, Abuav R, Narrowband ultraviolet B phototherapy for the treatment of steroid-refractory and steroid-dependent acute graft-versus-host-disease of the skin, J Am Acad Dermatol Oct. 2011;65(4):733-738.
Nakamura Kazuhiro, Central circuitries for body temperature regulation and feer, Am J Physiol Regul Integr Comp Physiol 301:R1207-R1228, 2001.
Kluger MJ, Vaughn LK, Fever and survival in rabbits infected with Pasteurella Multocida. J Physiol 282:243-251. 1978.
Kobayashi S, Hori A, Matsumura K, Hosokawa H. Pont: Heat-induced membrane depolarization of hypothalamic neurons: a putative mechanism of central thermosensitivity. Am J Physiol Regul Integ Comp Physiol 290:R1479-R1480, 2006.
Nakamura K. Blatteis CM. Fever: is it beneficial? Yale J Biol Med 59:107-116, 1986.
Al Ghumlas AK, Abdel Gader AG, Hussein MF, Al Haidary A, White JG, Effects of heat on camel platelet structure and functions—a comparative study with humans. Liu Q, Shonghua Wei.
Liu Q, Li C, Predictive value of myoglobin and D-dimer on severe heat stroke: a clinical analysis of 38 patients with severe heat stroke, Zhonghua Wei Zhong Bing Ji Jiu Yi Xue May 2019;31(5):594-597.
Becker JA, Stewart LK, Heat-Related Illness Am Fam Physician. Jun. 1, 2011;83(11):1325-1330.
Becker Glazer JL. Management of heatstroke and heat exhaustion. Am Fam Physician. 2005;71(11):2133-2140.
Marshall SW. Heat injury in youth sport. Br J Sports Med. 2010;44(1):8-12.
Pease S, Bouadma L, Kermarrec N, Schortgen F, Régnier B, Wolff M. Early organ dysfunction course, cooling time and outcome in classic heatstroke. Intensive Care Med. 2009;35(8):1454-1458.
Gabay C, Kushner I. Acute-phase proteins and other systemic responses to inflammation [published correction appears in N Engl J Med. 1999; 340(17):1376]. N Engl J Med. 1999;340(6):448-454.
Kiekkas P, Aretha D. Bakalis N, Karpouhtsi I, Marneras C, Baltopoulos GI. Fever Effects and Treatment in Critical Care: Literature Review Aust Crit Care, Aug. 2013:26(3):130-5.
Mink S, Schwarz U, Mudra R, Gugl C, Frohlich J, Keller E. Treatment of Resistant Fever: New method of Local Cerebral Cooling, Neurocrit Care, Aug. 2011;15(1):107-12.
DeFazio C, Skrifvars MB, Soreide E, Creteur J, Grejs AM, Kjergaard J, Laitio T, Nee J, Kirkegaard H, Taccone FS, Intravascular versus surface cooling for targeted temperature management after out-of-hospital cardiac arrest: an analysis of the TTH48 trial. Crit Care. 2019;23:61.
Janukavicius P, High H1N1 prevalence and mortality rates a concern. International SoS, Pandemics, https://pandemic.internationalsos.com/overview/, , CAMJ. Feb. 18, 2014;186(3): E104.
Dawwod FS, Iuliano AD, Reed C, Meltzer MI, Shay DK, Cheng PY, Bandaranayake D, Breiman RF, Brooks WA, Buchy P, Feikin DR, Fowler KB, Gordon A, Hien NT, Horby P, Huang WS, Katz MA, Krishnan A, Lal R, Montgomery JM, Molbak K, Pebody R, Presanis AM, Razuri H, Steens A, Tinoco YO, Wallinga J, Yu H, Vong S, Bresee J, Niddownson MA, Estimated global mortality associated with the first 12 months of 2009 pandemic influenza A H1N1 virus circulation: A modelling study, Lancet Infect Dis Sep. 2012;12(9):687-95.
Leduc JW, Barry MA, SARS, The first pandemic of the 21st Century. International SoS Mers-Covid. Overview, Emerg Infect Dis. Nov. 2004; 10(11):e26.
International SoS Mers-Cov. Overview, Https://pandemic.internationalsos.com/overview/mers-overview.
John Hopkins Coronavirus Resource Center, May 2020.
Fehr AR, Perlman S, Coronaviruses: An Overview of Their Replication and Pathogenesis, Coronaviruses: 2015;1282:1-23.
Su S, Wong G, Shi W, Liu J, Lai ACK, Zhou J, Liu W, Bi Y, Gao GF, Epidemiology, Genetic Recombination and Pathogenesis of Coronaviruses, Trends Microbiol. Jun. 2016 ;24(6):490-502.
National Academy of Sciences, Future pandemics pose massive risks to human lives, global economic security: New report. Science Daily, Jan. 13, 2016.

(56) References Cited

OTHER PUBLICATIONS

Madhav N, Oppenheim B, Gallivan M, Mulembakani P, Rubin E, Wolfe N, Jamison DT, Gelband H, Horton S, Jha P, Laxminarayan R, Mock CN, Nugent R, Pandemics: Risks, Impacts, and Mitigation. In Disease Control Priorities: Improving Health and Reducing Poverty. 3rd edition. Washington (DC): the International Bank for Reconstruction and Development/The Wordl Bank;Nov. 27, 2017. Chapter 17.

World Economic Forum, The Global Risks Report 2019, 14th Edition, International Monetary Fund 2018, World Economc Outlook Oct. 2018: Challenges to Steady Growth, Washington DC: IMF. https://www.imf.org/en/publivcations/weo.

Singer M, Deutschman CS, Seymour CW, Shankar-Hari M, Annane D, Bauer M, Bello,M R, Bernard GR, Chiche JD, Coopersmith CM, Hotchkiss RS, Levy MM, Marshall JC, Martin GS, Opan SM, Rubenfeld GD, van der Poll T, Vincent JL, Angus DC, The Third International Consensus Definitions for Sepsis and Septic Shock (Sepsis-3), JAMA. Feb. 23, 2016: 315(8):801-810.

Lake MA What we know so far: COVID-19 current clinical knowledge and research. Clin Med (Lond). Mar. 2020;20(2):124-127. doi: 10.7861/clinmed.2019-coron. Epub Mar. 5, 2020.

Chen N, Zhou M, Dong X, et al. Epidemiological and clinical characteristics of 99 cases of 2019 novel coronavirus pneumonia in Wuhan, China: a descriptive study. Lancet. 2020;395(10223):507-513.

Huang C, Wang Y, Li X, et al. Clinical features of patients infected with 2019 novel coronavirus in Wuhan, China. Lancet. 2020;395(10223):497-506.

Tang N, Li D, Wang X, Sun Z. Abnormal coagulation parameters are associated with poor prognosis in patients with novel coronavirus pneumonia. J Thromb Haemost. 2020;https://doi.org/10.1111/jth.14768.

Phang T., Genetic diversity and evolution of SARS-CoV-2. Infect Genet Evol. Jul. 2020;81:104260.

Bird Flu. [Retrieved on Oct. 26, 2021], Retrieved from the Internet <URL:https://pandemic.internationalsos.com/overview/BirdFluoverview>.

Wu X, Hu X, Hamblin MR, Ultraviolet blood irradiation: Is it time to remember "the cure that time forgot"?, J Photochem Photobiol B. Apr. 2016; 157:89-96.

Aslam B, Wang W, Arshad MI, Khurshid M, Muzammil S, Rasool MH, Nisar MA, Alvi RF, Aslam MA, Qamar MU, Salamat MKF, Baloch Z, Antibiotic resistance: a rundown of a global crisis, Infect Drug Resist 2018; 11:1645-1658.

Anderson DJ, Moehring RW, Sloane R, et al. Bloodstream infections in community hospitals in the 21st century: A Multicenter Cohort Study. PLOS ONE PlanetPJ, ed. 2014; 9:e91713. [PMC free article] [PubMed].

Gaieski DF1, Edwards JM, Kalian MJ, Carr BG. Benchmarking the incidence and mortality of severe sepsis in the United States. Crit Care Med. May 2013;41(5):1167-74.

Cassini A, Högberg LD, Plachouras D, Quattrocchi A, Hoxha A, Simonsen GS, Colomb-Cotinat M, Kretzschmar ME, Devleesschauwer B, Cecchini M, Ouakrim DA, Oliveira TC7, Struelens MJ, Suetens C, Monnet DL; Burden of AMR Collaborative Group. Attributable deaths and disability-adjusted life-years caused by infections with antibiotic-resistant bacteria in the EU and the European Economic Area in 2015: a population-level modelling analysis. Lancet Infect Dis. Jan. 2019;19(1):56-66. doi: 10.1016/31473-3099(18)30605-4. Epub Nov. 5, 2018.

World Health organization. Sepsis. Apr. 19, 2018.

Fleischmann C, Scherag A, Adhikari NK, Hartog CS, Tsaganos T, Schlattmann P, Angus DC, Reinhart K International Forum of Acute Care Trialists. Assessment of Global Incidence and Mortality of Hospital-treated Sepsis. Current Estimates and Limitations. Am J Respir Crit Care Med. Feb. 1, 2016;193(3):259-72.

National Vital Statistics Reports, vol. 68, No. 9, Jun. 24, 2019.

Health at a Glance: Europe 2018. Health Status. Main causes of mortality, pp. 88-89.

World Health Organization The top 10 causes of death May 24, 2018.

CDC. Estimated Influenza Illnesses, Medical visits, Hospitalizations, and Deaths in the United States 2018-2019 influenza season. 24/7 Saving lives.

Carnell ME, Taylor DR, Evaluation of inactivation methods for severe acute respiratory syndrome coronavirus in oncellular blood products, Transfusion Oct. 2006;46(10):1770-7.

Groner A, Broumis C, Fang R, Nowak T, Popp B, Schafer W, Roth NJ, Effective inactivation of a wide range of viruses by pasteurization, Transfusion. Jan. 2018; 58(1): 41-51.

Kalmar ID, Cay AB, Tignon M, Sensitivity of African swine fever virus (ASFV) to heat, alkalinity an peroxide treatment in presence or absence of porcine plasma, Vet Microbiol. Jun. 2018;219:144-149.

Yue C, Teitz S, Miyabashi T, Boiler K, Lewis-Ximenez LL, Baylis SA, Blumel J, Inactivation and Removal of Chikungunya Virus and Mayaro Virus from Plasma-derived Medical Products, Viruses Mar. 2019: 11(3): 234.

Houssein I, Wilcox H, Barron J, Effect of heat treatment on results for biochemical analysis of plasma and serum, Clin Chem. Dec. 1985;31(12):2028-30.

Huangfu C, Ma Y, Jia J, Lv M, Zhu F, Ma X, Zhang J, Inactivation of viruses by pasteurization at 600 C for 10 h with and without 40% glucose as stabilizer during a new manufacturing process of α2-Macroglobulin from Cohn Fraction IV, Biologicals. Mar. 2017;46:139-142.

Burnouf-Radosevich M, Burnouf T, Huart JJ, Inudstiral pasteurization of plasma and criteria of quality. Rev Fr Transfus Hemaobiol. Jan. 1993;36(1):93-102.

Chandra S, Groener A, Feldman F. Effectiveness of alternative treatments for reducing potential viral contaminants from plasma-derived products Thromb Res. Mar. 1, 2002;105(5):391-400.

In Seop K, Choi Yong Woon, Kang Y, Mo Sung H, Shin JS, Dry-Heat Treatment Process for Enhancing Viral Safety of an Antihemophilic Factor VIII Concentrate Prepared from Human Plasma. J Microbiol. Blotechnol. (2008),18(5).997-1003.

Huangfu C, Zhao C, Lv M, Jia J, Zhu F, Wang R, Ma Y, Zhang J, Inactivation of viruses during a new manufacturing process of α2-macroglobulin from Cohn Fraction IV by dry-heat treatment. Transfusion. Sep. 2016;56(9):2274-7.

Kumar V, Lockerbie O, Keil SD, Ruane PH, Platz MS, Martin CB, Ravanat JL, Cadet J, Goodrich RP Riboflavin and UV-light based pathogen reduction: extent and consequence of DNA damage at the molecular level. Photochem Photobiol. Jul.-Aug. 2004;80:15-21.

Riley RL, Nardell EA, Clearing the Air: The Theory and Application of Ultraviolet Air Disinfection, Am Rev of Resp Dis 139:1286-1294, 1992.

Memarzadeh F. Olmsted RN, Bartley JM, Applications of ultraviolet germicidal irradiation disinfection in health care facilities: Effective Adjunct, but not stand-alone technology, Am J Infect Control 20110;38:S13-24.

Eickmann M, Gavemann U, Handke W, Tolksdorf F, Feichenbeerg S, Muller TH, Saltsaqm A, Inactivation of Ebola virus and Middle East respiratory syndrome coronavirus in platelet concentrates and plasma by ultraviolet C light and methylene blue plus visible light, respectively, transfusion. Sep. 2018;58(9):2202-2207.

Eickmann M, Gravemann U, Handke W, Toksdorf F, Reichenberg S, Muller TH, Seltsam A, Inactivation of three emerging viruses-sever acute respiratory syndrome coronavirus, Crimean-Congo Haemor-rhagin fever virus and Nipah Virus—in platelet concentrates by ultraviolet C light ad in plasma by methylene blue plus visible light. Vox Sang Apr. 2020; 115(3): 146-151.

Keil SD, Bowen R, Marschner S. Inactivation of Middle East respiratory syndrome coronavirus (MERS-CoV) in plasma products using a riboflavin-based and ultraviolet light-based photochemical treatment Transfusion. Dec. 2016;56(12):2948-2952.

Keil SD, Ragan I, Yonemura S, Harson L, Dart NK, Bowen R, Inactivation of severe acute respiratory syndrome coronavirus 2 in plasma and platelet products using a riboflavin and ultraviolet light-based photochemical treatment. Vox Sang. Apr. 20, 2020.

Hindawi SI, Hashem AM, Damanhouri GA, El-Kafrawy SA, Tolah AM, Hassan AM, Azhar EI, Inactivation of Middle East respiratory

(56) References Cited

OTHER PUBLICATIONS syndrome-coronavirus in human plasma using amotosalen and ultraviolet A light, Transfusion. Jan. 2018;58(1):52-59.

Duan SM, Zhao XS, Sen RF, Huang JJ, Pi GH, Zhang SX, Han J, Bi SL, Ruan L, Dong XP; SARS Research Team. Stability of SARS coronavirus in human specimens and environment and its sensitivity to heating and UV irradiation. Biomed Environ Sci. Sep. 2003;16(3):246-55.

Ettinger A, Miklauz MM, Bihm DJ, Maldonado-Codine G, Goodrich RP, Preparation of cryoprecipitate from riboflavin and UV light-treated plasma. Transfus Apher Sci. Apr. 2012;46(2):153-8.

Smith J, Rock G, Protein quality in Mirasol pathogen reduction technology-treated, apheresis-derived fresh-frozen plasma. Transfusion. Apr. 2010;50(4):926-31.

* cited by examiner

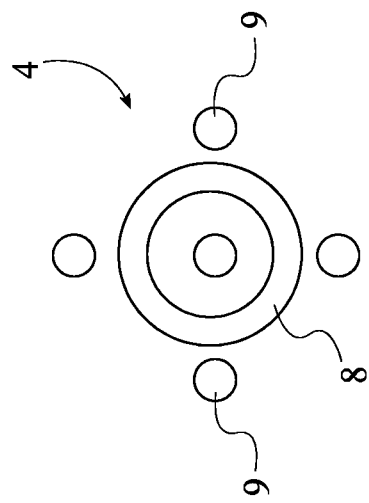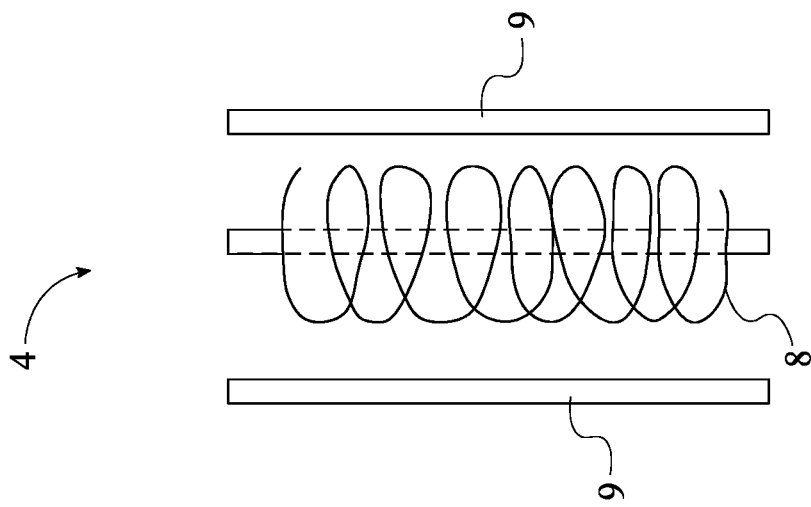
FIG. 5

(A) Providing an input peristaltic pump, at least one apheresis device, at least one plasma-treating system, and an output peristaltic pump, wherein the input peristaltic pump, the apheresis device, the plasma-treating system, and the output peristaltic pump are in fluid communication with each other, and wherein the plasma-treating system includes at least one primary ultraviolet light (UVL) device, at least one heating device, and at least one cooling device

↓

(B) Pumping a quantity of initial blood out of a patient into the apheresis device with the input peristaltic pump

↓

(C) Separating the quantity of initial blood into a quantity of plasma, a quantity of leucocytes, and a quantity of red blood cells with the apheresis device

↓

(D) Heating the quantity of plasma to a specified temperature with the heating device

↓

(E) Irradiating the quantity of plasma with the primary UVL device

↓

(F) Cooling the quantity of plasma to a specified temperature with the cooling device

↓

(G) Pumping and mixing the quantity of plasma, the quantity of leucocytes, and the quantity of red blood cells as a quantity of treated blood into the patient with the output peristaltic pump

FIG. 6

SYSTEM AND METHOD FOR FACILITATING EXTRACORPOREAL INACTIVATION OF PATHOGENS OF BLOOD PRODUCTS

The current application claims a priority to the U.S. Provisional Patent application Ser. No. 63/111,867 filed on Nov. 10, 2020.

FIELD OF THE INVENTION

The present invention relates generally to a field of extracorporeal blood circulation devices. More specifically, the present invention is a system and method for facilitating the extracorporeal inactivation of pathogens of blood products.

BACKGROUND OF THE INVENTION

Over the years, many apparatuses have been designed for extracorporeal inactivation of pathogens in plasma and blood products using physical elements, such as, radiation, changes in physical environment (such as, oxidation of the plasma and the blood products at various levels of oxygen), or filters to capture pathogens or toxins circulating in blood, and photosensitizers to sensitize pathogens before exposure to ultraviolet light (UVL) or other radiation sources. Even though some of these apparatuses could have been used to treat systemic infections for which there is no effective treatments available like epidemics or pandemics caused by viruses, or sepsis caused by antibiotic resistant pathogens, practically none of them are in use for this purpose, because of the lack of studies to demonstrate safety and efficacy of such apparatuses have not been performed. This likely occurred because the clinical indications for the use of such apparatuses may not have been clearly defined and would not have justified the high cost of the validation studies. Further, because of the lack of effective treatments, the treatment consists on supporting the major organs' functions with the hope that the patient's own immune system overcomes the infection. However, this treatment often fails to decrease the mortality.

In addition to it, there have been several instances where the use of a suitable apparatus for extracorporeal inactivation of pathogens in plasma and blood products would have been proved effective in dealing with global infectious disease outbreaks or pandemics like the many that occurred during the past century that affected millions of people and caused a staggering high mortality, unemployment and economic losses thorough world. These outbreaks included the Spanish flu pandemic of 1918, which affected 30% of the world population and caused a 50% mortality; the Asian Flu in 1957 caused by the influenza A/H2N2 strain; the Hong Kong Flu of 1968 caused by the A/H3N2 strain; the Swine Flu of 2009 caused by the A/H1N1 strain, which caused an estimated 284,000 death worldwide (R1-R2); the Severe Acute Respiratory Syndrome Coronavirus (SARS-Co) in 2003 affecting 26 countries (R3); the Middle Eastern Respiratory Syndrome Coronavirus (MERS-CoV) (R4), and the Coronavirus CoVid-19 or SARS-CoV-2 pandemic in 2019 that affected over 6 million people in over 180 countries (R5) and has caused over 600,000 deaths (R6-R7). Furthermore, it is inevitable that pandemics and single or multiple epidemics will occur on a regular basis in the future because of increased global travel, integration, urbanization and intentional or accidental distribution of pathogens that could or could not have been genetically modified and that these infections will kill millions of people and may cause trillions of dollars of economic damage (R8-R10). High mortality caused by the pandemics or endemics, especially the Covid-2 pandemic, occurred because in many patients the infections affected many organ functions or caused an excessive inflammatory response with severe single or multiple organ damage or cytokines storm (R11) and the lack of effective treatments available (R12-R15).

Even if effective treatments and/or vaccines are developed to treat and prevent these infections, they may not be useful if the viruses spontaneously mutate which is often the case, such as flu, Covid-19 (R16) or in outbreaks of known pathogens that rarely affect humans, such as bird flu viruses A strains H5N1, H7N9 which have affected hundreds of peoples or the viruses H5N6 and H1N8 that have caused occasional infections (R17) or in outbreaks of unknown or genetically modified pathogens. Further, the patients with severe antibiotic resistant infections with bacteremia for which there is no effective treatment available could also be treated with the apparatus disclosed in the present disclosure. These infections cause a two-fold higher mortality than antibiotic sensitive infections, considerable longer hospital admissions, and it has been estimated that they could kill an extra 10 million people across the world every year by 2050 and could cause an economic loss of $100 trillion per year (R18-R19).

In the US, about 23% of blood stream infections are caused by multiple drug resistant bacteria which cause a 25% mortality (R20) and at least 894,000 cases of severe infections occur yearly (R21). In the European Union, about 700,000 cases have been reported in 2015 (R22). Furthermore, 30 million cases of sepsis were reported worldwide in 2015 with a mortality of about 6 million (R23), or of 17% and 25% among hospitalized patients with sepsis or severe sepsis, respectively (R24).

Finally, for the patients with severe infections of non-epidemic occurrences, if they are accompanied by viremia or bacteremia and there is no effective treatment available, i.e. many viral lower respiratory tract infections, which are the cause of many of the 55000 deaths per year in the US (recorded as influenza-pneumonia) (R25), the 440,000 deaths per year in the European Union (including COPD) (R26), and of the 3 million deaths per year worldwide and are considered the most deadly communicable disease worldwide (R27-R28), the use of a suitable apparatus for extracorporeal inactivation of pathogens in plasma and blood products would have been proved effective.

Existing apparatuses for facilitating extracorporeal sterilization and cooling of blood products are deficient with regard to several aspects. For instance, current apparatuses do not use heat and ultraviolet light for the treatment on continuous flowing plasma to inactivate viruses and other pathogens which are present in the plasma to decrease the severity of the infection and of inflammation and expose whole blood, leucocytes or buffy coat to UVL, to modulate the immuno-response. Further, current apparatuses do not decrease or raise the plasma temperature to normal in patients with fever. Furthermore, current apparatuses do not facilitate inducing hypothermia in patients with acute brain injury without sepsis. Moreover, current apparatuses do not inactivate pathogens in the patients or modulate the excessive inflammatory response that is usually present in the patients that are seriously ill.

Therefore, there is a need for improved apparatuses, methods, systems, and devices for facilitating extracorporeal sterilization and cooling of blood products that may overcome one or more of the above-mentioned problems and/or limitations.

SUMMARY OF THE INVENTION

This summary is provided to introduce a selection of concepts in a simplified form, that are further described below in the Detailed Description. This summary is not intended to identify key features or essential features of the claimed subject matter. Nor is this summary intended to be used to limit the claimed subject matter's scope.

According to some embodiments, an apparatus for facilitating extracorporeal sterilization and cooling of blood products, is disclosed. Further, the apparatus may include at least one circuit of tubes. Further, the at least one circuit of tubes may include a catheter to suction blood from a large vein, a similar catheter to return blood to a vein (or one double lumen catheter to suction and return blood), and one or more tubes of the at least one circuit of tubes to transport the blood and/or blood plasma through the heat, UVL and cooling components, and at least one input peristaltic pump to move the blood from a patient towards at least one apheresis component. Further, the at least one apheresis device may separate the blood plasma, leucocytes and/or a buffy coat and red blood cells and may include (components not shown in the drawing) a peristaltic pump with rollers to propel blood drawn from the patient, a filter or centrifuge to separate the plasma from one or more blood cells, a container for each of separated components thereof of the blood, and devices to measure the blood and plasma flow rate. Further, an output peristaltic pump may be added to propel the plasma at a steady flow rate. Further, at least one heating device may heat the blood plasma up to 60° C. (10), located between the apheresis device and a primary ultraviolet light (UVL) device. Further, the heating device may include a coiled tube to transport the plasma that may be enclosed in a container full of water or other heat adsorbing liquid. Further, the primary UVL device may include one or more sets of two thin parallel membranes in close proximity to and facing each other for allowing circulation of a thin layer of the blood plasma between the membranes. Further, at least one cooling device may facilitate decreasing of the plasma temperature to a normal range or lower. Further, the cooling device may include a coiled tube that may transport the plasma enclosed in a container full of cold water or other liquid of low freezing point. Further, a first segment of the one or more tubes may facilitate transporting of the one or more blood cells separated by the apheresis device to merge with a second segment of the one or more tubes transporting the blood plasma which may be treated with heat and UVL, to reconstitute the blood. Further, a third segment of the one or more tubes to return reconstituted blood to the patient, in an instance, may include a usage of a peristaltic pulse pump with rollers synchronized with the peristaltic pump and the additional peristaltic pump to propel the reconstituted blood towards the patient. Further, the apparatus may include at least one blood-treating system. Further, the at least one blood-treating system may be disposed of in between a needle configured for suctioning of the blood from the patient and the apheresis device. Further, the at least one component for treating whole blood with UVL may include a reservoir to store the blood, a gauge to measure the volume stored in the reservoir, a shut off valve that closes after the desired volume of the blood is in the reservoir, a separate peristaltic pump to propel the blood towards a separate UVL chamber. Further, in an instance, the apparatus may include at least one component for treating the leucocytes and/or the buffy coat instead of the at least one component for treating of whole blood with UVL. Further, the at least one component for treating the leucocytes and/or the buffy coat may be similar to the at least one component for treating of whole blood with UVL.

Further, the apparatus may include one or more thermometers. Further, the one or more thermometers may monitor and/or regulate temperature of the blood plasma. Further, each thermometer of the one or more thermometer may be disposed of in the heating liquid reservoir, in the at least one heating component, adjacent to the at least one heating component, at the at least one UVL component, adjacent to the at least one UVL component, at the at least one cooling component, at the cooling liquid reservoir, adjacent to the at least one cooling component, adjacent to the at least one UVL component to treat whole blood and adjacent to the at least one UVL component to treat the leucocytes and/or the buffy coat. Further, the apparatus may include one or more thermostats. Further, each thermostat of the one or more thermostats may be disposed of at the heating liquid reservoir, at the at least one heating component, at the at least one UVL component, at the at least one cooling component, and at the cooling liquid reservoir.

Both the foregoing summary and the following detailed description provide examples and are explanatory only. Accordingly, the foregoing summary and the following detailed description should not be considered to be restrictive. Further, features or variations may be provided in addition to those set forth herein. For example, embodiments may be directed to various feature combinations and subcombinations described in the detailed description.

BRIEF DESCRIPTION OF THE DRAWINGS

FIG. 5 is a pair of diagrams illustrating another embodiment of the primary UVL device.

FIG. 6 is a flowchart illustrating the overall process for the method of the present invention.

DETAIL DESCRIPTIONS OF THE INVENTION

All illustrations of the drawings are for the purpose of describing selected versions of the present invention and are not intended to limit the scope of the present invention.

Figure 1:
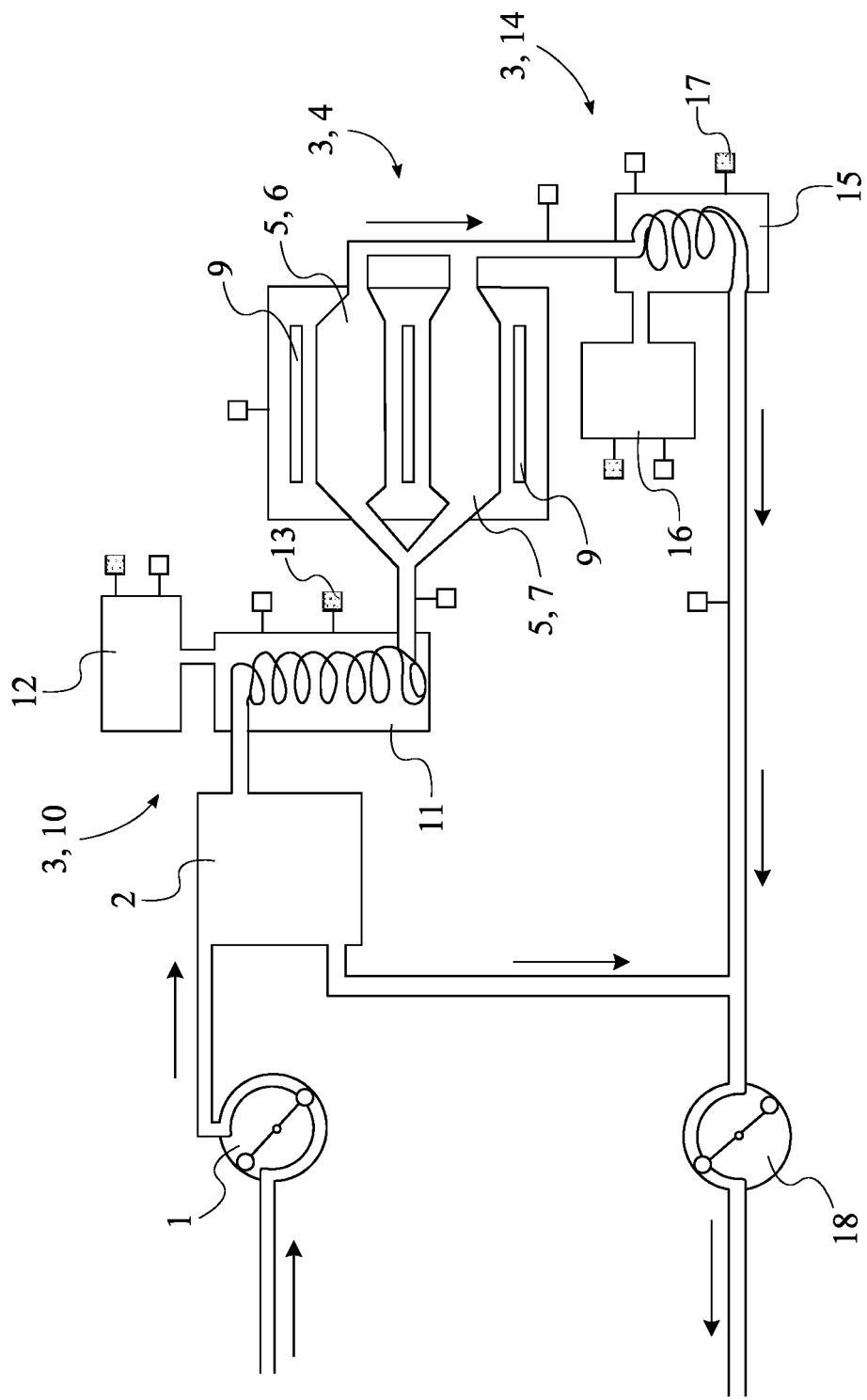
FIG. 1 is a diagram illustrating the overall system of the present invention.

In reference to FIGS. 1 through 15, the present invention is a system and method for facilitating the extracorporeal inactivation of pathogens of blood products. With reference to FIG. 1, the system of the present invention includes an input peristaltic pump 1, at least one apheresis device 2, at least one plasma-treating system 3, and an output peristaltic pump 18 (Step A). The input peristaltic pump 1, the apheresis device 2, the plasma-treating system 3, and the output peristaltic pump 18 are in fluid communication with each other. The plasma-treating system 3 includes at least one primary ultraviolet light (UVL) device 4, at least one heating device 10, and at least one cooling device 14. The input peristaltic pump 1 facilitates the flow of blood from a patient through the system of the present invention. The input peristaltic pump 1 may include at least two rollers and the two rollers, in an instance, may be in similarity with rollers of one or more peristaltic pumps used in dialysis machines or apheresis machines. Further, in some embodiments, the input peristaltic pump 1 may include one or more rollers in addition to the two rollers. The one or more rollers may decrease a change in velocity and/or turbulence of the flowing of the blood and/or the blood plasma. Further, the input peristaltic pump 1, in an instance, may be positioned close to a first lumen catheter that suctions blood from one or more large veins of the patient. The apheresis device 2 facilitates separating of the blood plasma from one or more blood cells. The apheresis device 2 may separate the one or more blood cells (such as red cells, white cells, platelets and/or the buffy coat) from the blood plasma based on density of each type of blood cell of the one or more blood cells. Further, the separating of plasma, in an instance, may be based on a continuous flow centrifugation and/or filtering. Further, the apheresis device 2, in an instance, may include a peristaltic pump, a centrifuge, and a reservoir. Further, the reservoir may store the one or more blood cells. Further, the peristaltic pump of the apheresis device 2 may allow a slow blood flow rate, in an instance, in a range of 100-200 mL/min. Further, the slow blood flow rate, in an instance, may result in a plasma flow rate, in an instance, in a range of 50-100 mL/min. The plasma-treating system 3 inactivates pathogens within the plasma that is separated from the one or more blood cells. The output peristaltic pump 18 facilitates the flow of blood from the system of the present invention and back to the patient. The output peristaltic pump 18 may include at least two rollers and the two rollers, in an instance, may be in similarity with rollers of one or more peristaltic pumps used in dialysis machines or apheresis machines. Further, in some embodiments, the output peristaltic pump 18 may include one or more rollers in addition to the two rollers. The one or more rollers may decrease a change in velocity and/or turbulence of the flowing of the blood and/or the blood plasma. Further, the output peristaltic pump 18, in an instance, may be positioned close to a second lumen catheter that returns blood to one or more large veins of the patient.

The input peristaltic pump 1, the apheresis device 2, the plasma-treating system 3, and the output peristaltic pump 18 are in fluid communication with each other through a circuit of tubes. One or more tubes of the circuit of tubes may include shapes such as, but are not limited to, cylindrical, cuboidal, etc. Further, the cylindrical shape of the one or more tubes of the circuit of tubes, in an instance, may include a small internal cross-sectional diameter such as, but is not limited to, in a range of 1-2 mm. The cuboidal shape of the one or more tubes of the circuit of tubes, in an instance, may include cross-sectional dimensions such as, but are not limited to, 1 mm in height and 2 mm in width. The one or more tubes, in an instance, may include a thin and malleable wall. Moreover, the one or more tubes, in an instance, may include a length such as, but is not limited to, in a range of 1-2 meters. As mentioned previously, the plasma-treating system 3 includes the primary UVL device 4, the heating device 10, and the cooling device 14. The heating device 10 heats the plasma separated from the one or more blood cells to a specific temperature. The UVL device irradiates the plasma. The cooling device 14 cools the plasma to a specific temperature.

With reference to FIG. 6, the method of the present invention follows an overall process that facilitates the extracorporeal inactivation of pathogens of blood products. The input peristaltic pump 1 pumps a quantity of initial blood out of a patient into the apheresis device 2 (Step B). In more detail, in conjunction with the first lumen catheter, the input peristaltic pump 1 facilitates the flow of the quantity of initial blood from the patient and into the apheresis device 2 through the circuit of tubes. The apheresis device 2 separates the quantity of initial blood into a quantity of plasma, a quantity of leucocytes, and a quantity of red blood cells (Step C). In more detail, the apheresis device 2 separates the quantity of plasma in preparation to treat the quantity of plasma. Before the quantity of plasma is treated, the heating device 10 heats the quantity of plasma to a specified temperature (Step D). In more detail, heating the quantity of plasms inactivates viruses by denaturing the secondary structures of proteins and altering the proteins involved in attachment and replication within a host cell and its effect depends on the temperature level and duration of exposure. The specified temperature is a maximum of 140 degrees Fahrenheit or 40 degrees Celsius to 60 degrees Celsius. Further, heating the quantity of plasma is for the purpose of sensitizing pathogens such as in pasteurization (140 degrees Fahrenheit for up to 10 hours) dry heat of up to 212 degrees Fahrenheit for 30 min, 176 degrees Fahrenheit for 72 hours or 60 degrees Celsius for 10-30 minutes. Based on the above studies, it is assumed that heating the quantity of plasma up to 140 degrees Fahrenheit increases the inactivation of pathogens by UVL at least 50%. The primary UVL device 4 irradiates the quantity of plasma (Step E). In more detail, irradiating the quantity of plasma inactivates pathogens in the quantity of plasma. The primary UVL device 4 emits a plurality of shortwaves. Each of the plurality of shortwave ranges from 280 nanometers to 360 nanometers. After the quantity of plasma is irradiated, the cooling device 14 cools the quantity of plasma to a specific temperature (Step F). In more detail, cooling the quantity of plasma allows the quantity of plasma to be safely returned to the patient. The specified temperature is at a maximum of 98 degrees Fahrenheit which aims to match the normal temperature of a human. Finally, the output peristaltic pump 18 pumps and mixes the quantity of plasma, the quantity of leucocytes, and the quantity of red blood cells as a quantity of treated blood into the patient (Step G). In more detail, a treated quantity of plasma is mixed with the quantity of leucocytes, and the quantity of red blood cells to produce the quantity of treated blood. The quantity of treated of blood then flows from the system into the patient in order to treat the patient.

Figure 7:
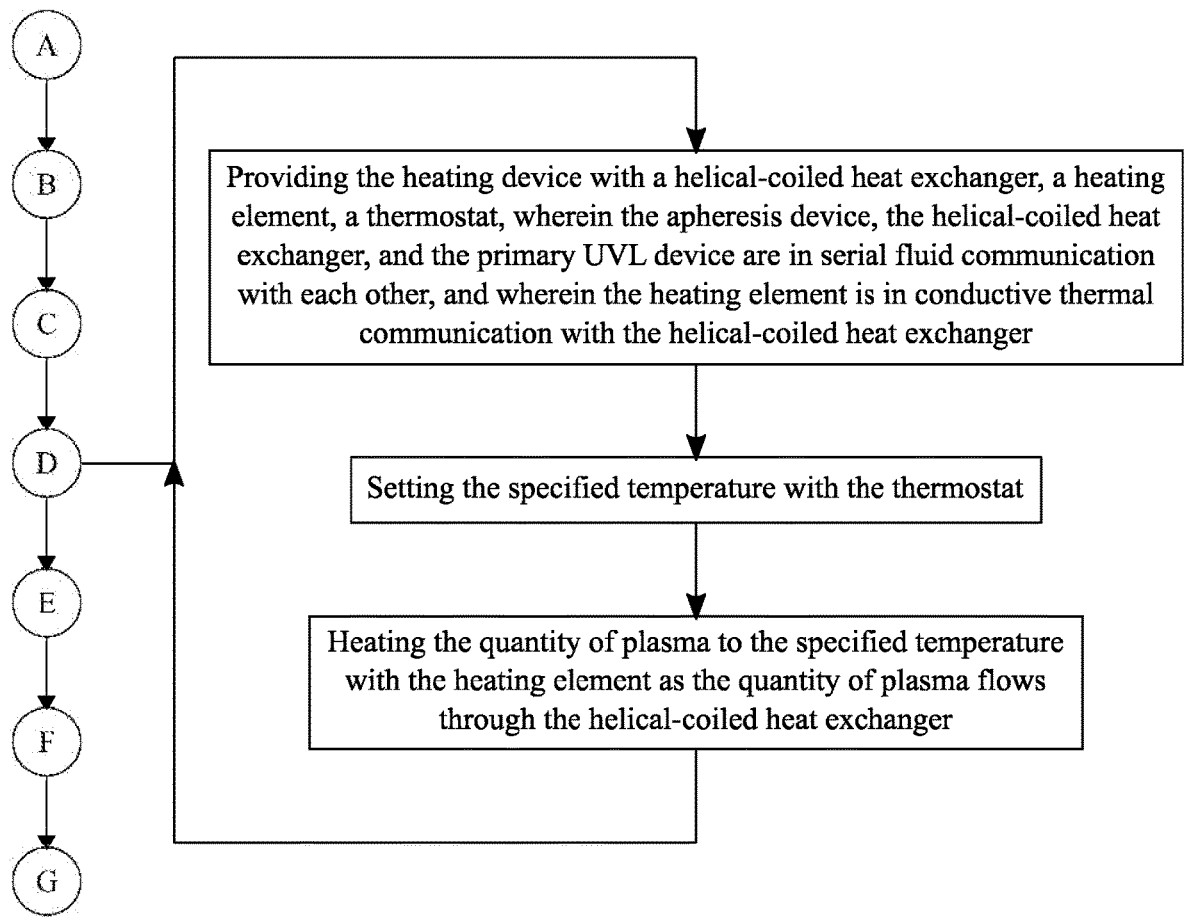
FIG. 7 is a flowchart illustrating the subprocess on how the quantity of plasma is heated.

In order for the heating device 10 to effectively heat the quantity of plasma to the specified temperature and with reference to FIG. 7, the following subprocess is executed. The heating device 10 is provided with a helical-coiled heat exchanger 11, a heating element 12, and a thermostat 13. The apheresis device 2, the helical-coiled heat exchanger 11, and the primary UVL device 4 are in serial fluid communication with each other, and the heating element 12 is in conductive thermal communication with the helical-coiled heat exchanger 11. The helical-coiled heat exchanger 11, in an instance, may include a receptacle. The receptacle may be configured to store the heating element 12 (such as, water) that may reach a boiling point corresponding to a boiling point of the heating element 12. The receptacle may include a coiled tube such that the coiled tube may facilitate transporting of the quantity of plasma based on the heating element 12 in the receptacle. The heating of the heating element 12, in an instance, may be facilitated based the one or more electrical resistances. The heating element 12 in the receptacle, in an instance, may be heated based on at least one first electrical resistance of the one or more electrical resistances in a reservoir adjacent to the receptacle. Further, in some embodiments, the reservoir may include a peristaltic pump such and that peristaltic pump may facilitate circulating of the heating element 12 between the reservoir and the receptacle. Further, the quantity of plasma stored in the receptacle, in an instance, may be heated based on at least one alternate means, such as, but is not limited to, at least one second electrical resistance of the one or more electrical resistances placed inside the receptacle. The coiled tube, in an instance, may include a small diameter such as, but is not limited to, in a range of 1-2 millimeters. A length of the coiled tube, in an instance, may be in a range of 1-2 meters. The coiled tube may be disposed of in the receptacle. The coiled tube may include at least one type of material such that the at least one type of material may be characterized by one or more properties such as, but are not limited to, hardened, and heat resistant. The at least one type of material may include, but are not limited to, plastic, metal, or glass. The thermostat 13 is used to measure and regulate the temperature within the helical-coiled heat exchanger 11. The thermostat 13 sets the specified temperature. In more detail, a user can control the thermostat 13 or the thermostat 13 can automatically set the temperature within the helical-coiled heat exchanger 11 to the specified temperature. The heating element 12 heats the quantity of plasma to the specified temperature as the quantity of plasma flows through the helical-coiled heat exchanger 11. Thus, the heating device 10 effectively heats the quantity of plasma to the specified temperature.

Figure 8:
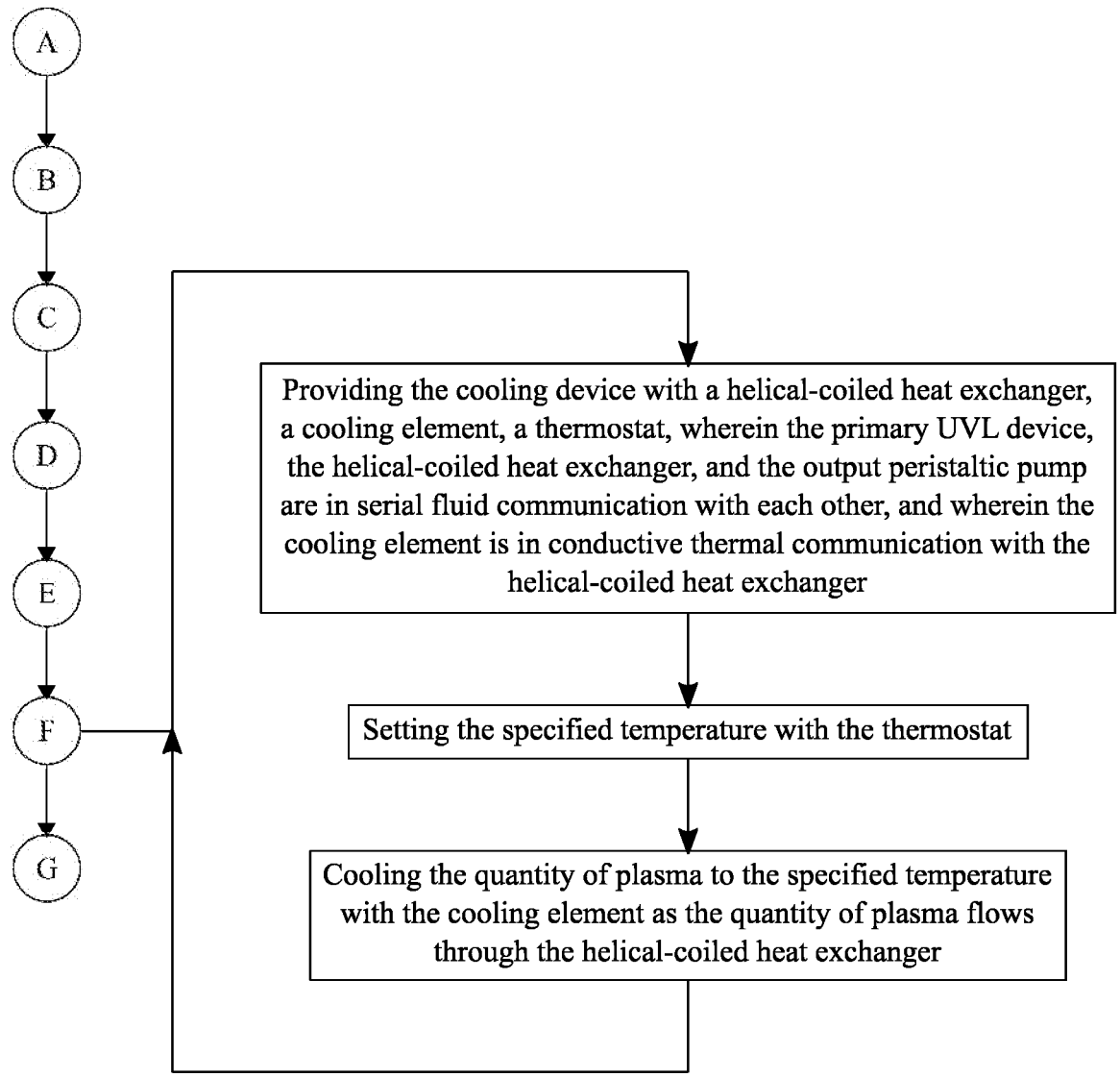
FIG. 8 is a flowchart illustrating the subprocess on how the quantity of plasma is cooled.

In order for the cooling device 14 to effectively cool the quantity of plasma to the specified temperature and with reference to FIG. 8, the following subprocess is executed. The cooling device 14 is provided with a helical-coiled heat exchanger 15, a cooling element 16, and a thermostat 17. The primary UVL device 4, the helical-coiled heat exchanger 15, and the output peristaltic pump 18 are in serial fluid communication with each other, and the cooling element 16 is in conductive thermal communication with the helical-coiled heat exchanger 15. The helical-coiled heat exchanger 15 may include a receptacle (or a chamber). The receptacle may store the cooling element 16 such that the cooling element 16 may reach low temperatures (low freezing point) in order to cool the quantity of plasma to the specified temperature. The receptacle may include a coiled tube. The coiled tube may transport the quantity of plasma, and in an instance, may possess characteristics similar to the coiled tube of the helical-coiled heat exchanger 15 of the heating device 10. The coiled tube in the receptacle of the at least one cooling component may include at least one type of biocompatible material. At least one type of material may include material such as, but is not limited to, PVC such that the coiled tube may not be heat-resistant. The at least one cooling component may include a cooling reservoir in order to cool the cooling element 16, and a pump to move the cooling element 16 from the cooling reservoir to the receptacle. Cooling, in an instance, may be facilitated using methods similar to methods used in refrigeration or a heat exchanger. The thermostat 17 sets the specified temperature. In more detail, a user can control the thermostat 17 or the thermostat 17 can automatically set the temperature within the helical-coiled heat exchanger 15 to the specified temperature. The cooling element 16 cools the quantity of plasma to the specified temperature as the quantity of plasma flows through the helical-coiled heat exchanger 15. Thus, the cooling device 14 effectively cools the quantity of plasma to the specified temperature.

Figure 9:
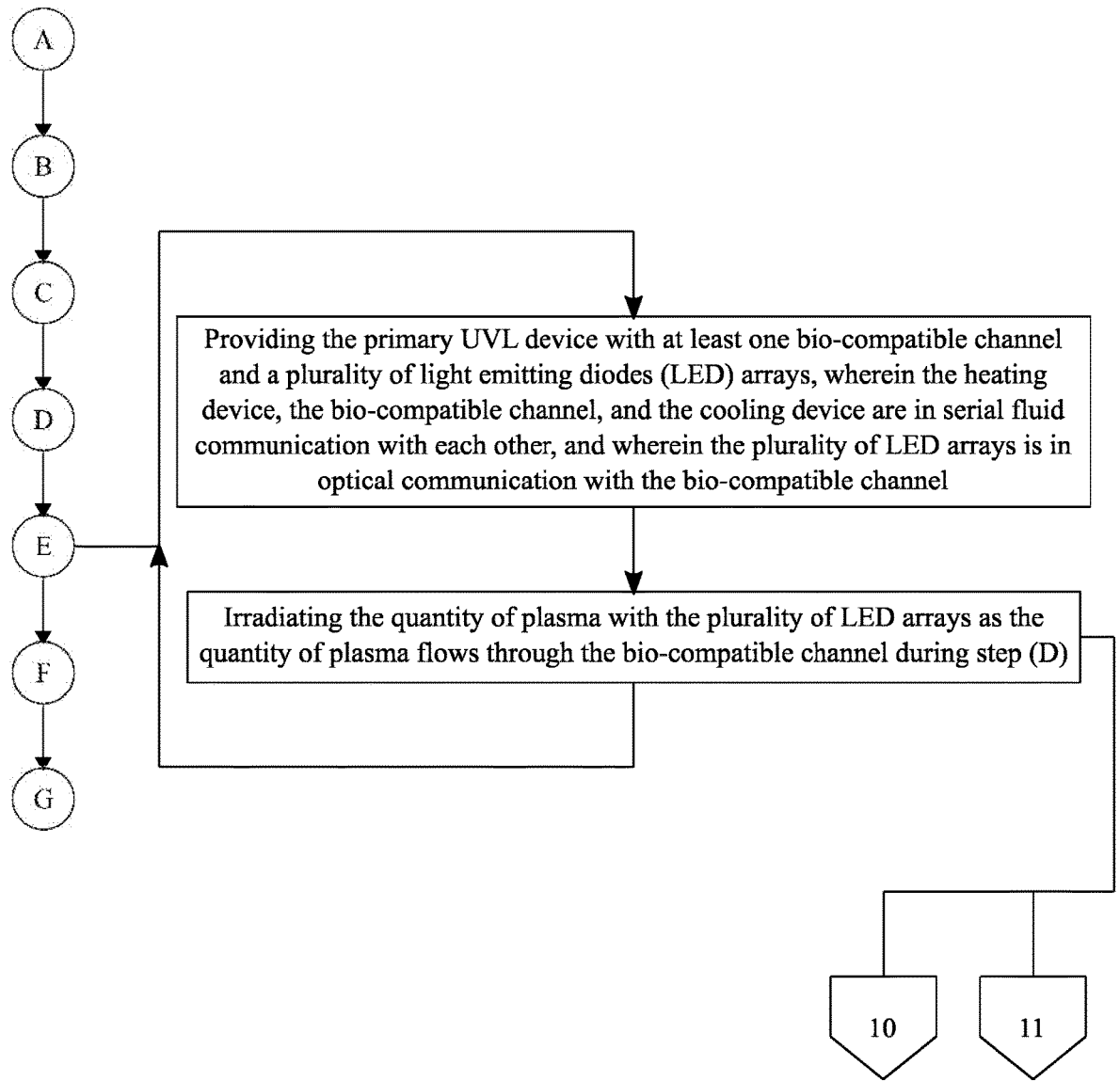
FIG. 9 is a flowchart illustrating the subprocess on how the quantity of plasma is irradiated.

In order for the primary UVL device 4 to effectively irradiate the quantity of plasma and with reference to FIG. 9, the following subprocess is executed. The primary UVL device 4 is provided with at least one bio-compatible channel 5 and a plurality of light emitting diodes (LED) arrays 9. The heating device 10, the bio-compatible channel 5, and the cooling device 14 are in serial fluid communication with each other, and the plurality of LED arrays 9 are in optical communication with the bio-compatible channel 5. Preferably, the primary UVL device 4 emits a plurality of shortwaves, and the wavelength of each of the plurality of shortwaves ranges from 280 nanometers to 360 nanometers. The plurality of LED arrays 9 may use semiconductors to emit UVL. Further, the plurality of LED arrays 9 in an instance, may either facilitate adjustable wavelength emissions or may not facilitate adjustable wavelength emissions. Further in other embodiments, the primary UVL device 4 may use one or more UVL sources which, in an instance, may include carbon lamps, or mercury vapor lamps. Further, an electrical-to-UVC conversion efficiency of the plurality of LED arrays 9 may be lower than that of the mercury vapor lamps, as a result of which a reduced size of the mercury vapor lamps may allow integration of the mercury vapor lamps into one or more medical devices. Further, in an instance, low pressure lamps may offer high efficiencies (for example, 35% UVL), but low power (for example, 1 W/cm power density (power per unit of arc length)). The plurality of LED arrays 9 irradiates the quantity of plasma as the quantity of plasma flows through the bio-compatible channel 5 during Step D. Thus, the primary UVL device 4 effectively irradiates the quantity of plasma with the plurality of LED arrays 9.

Figure 4:
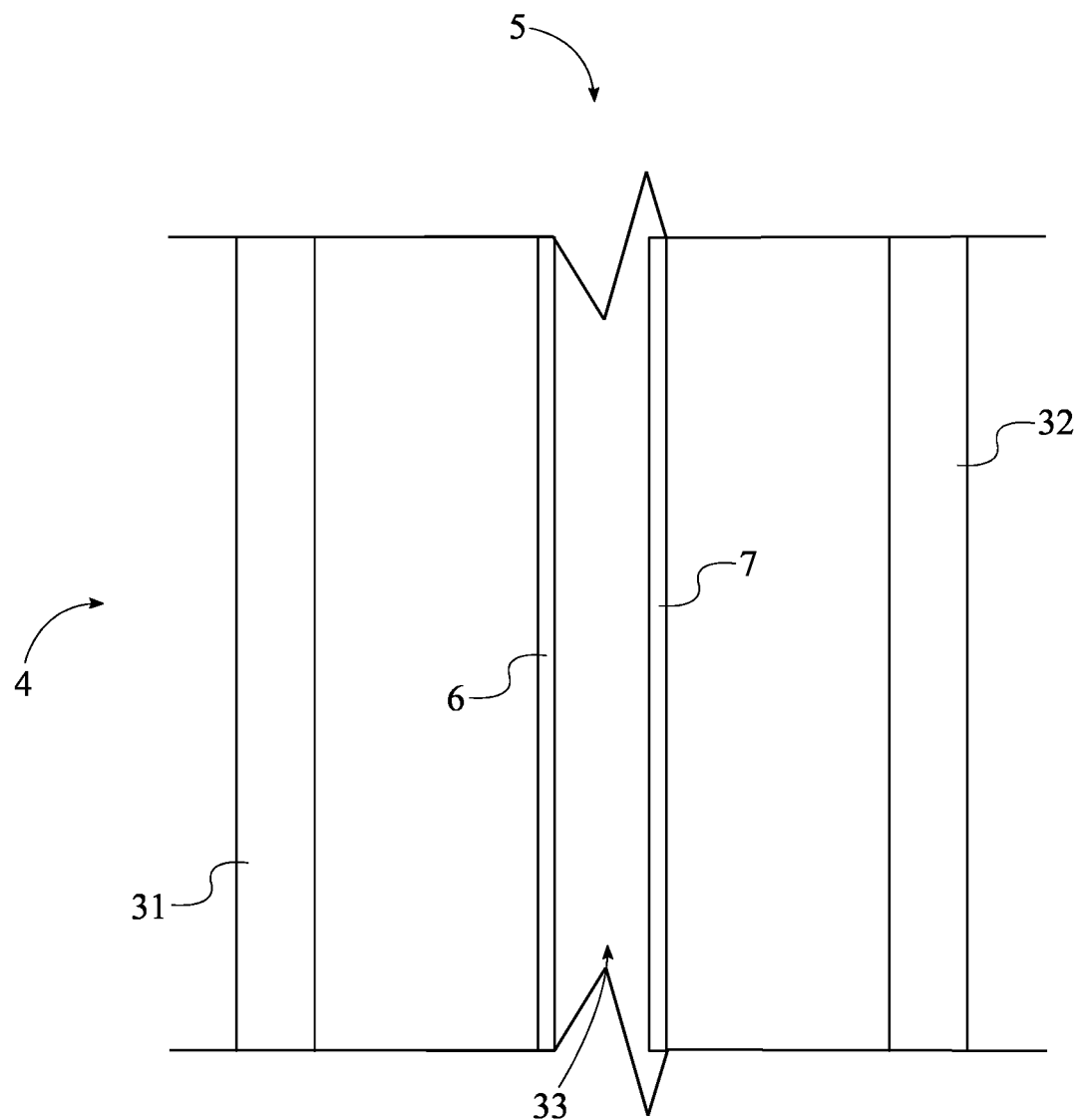
FIG. 4 is a diagram illustrating one embodiment for the primary UVL device.
Figure 10:
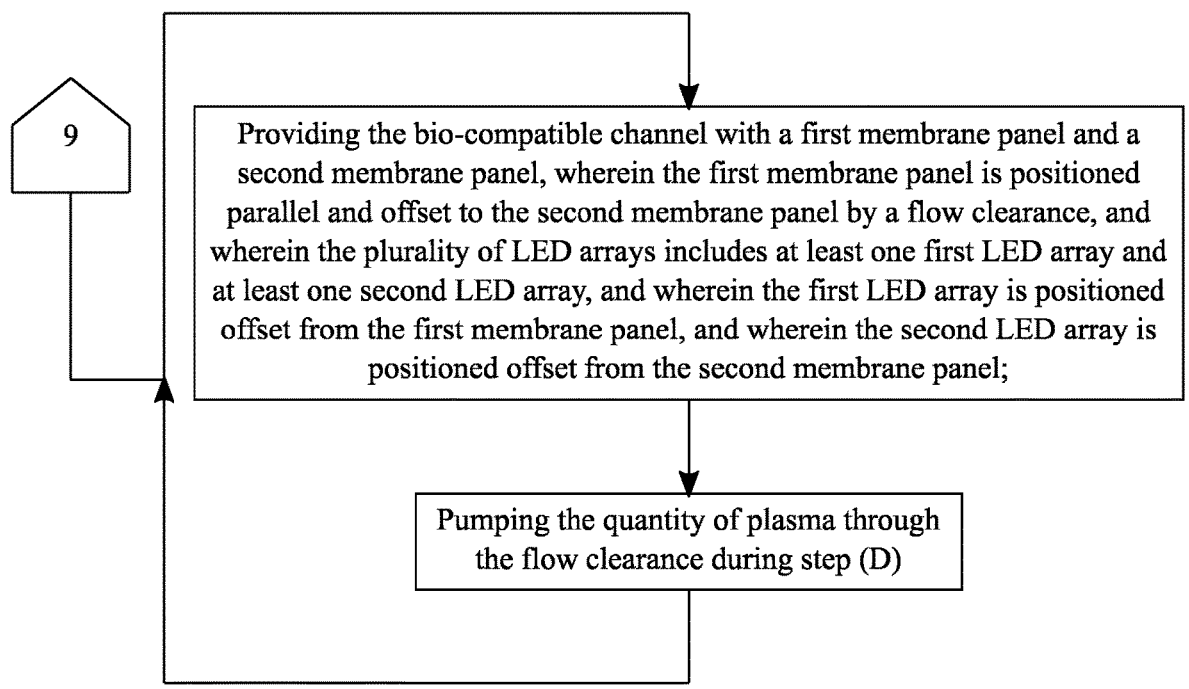
FIG. 10 is a flowchart illustrating the subprocess on how the quantity of plasma flows through the bio-compatible channel.

In order for the quantity of plasma to smooth flow through the bio-compatible channel 5 and with reference to FIGS. 4 and 10, the following subprocess is executed. The primary UVL device 4 may further include a receptacle. The receptacle houses the bio-compatible channel 5 which is provided with a first membrane panel 6 and a second membrane panel 7. The first membrane panel 6 is positioned parallel and offset to the second membrane panel 7 by a flow clearance 33. The plurality of LED arrays 9 includes at least one first LED array 31 and at least one second LED array 32. The first LED array 31 and the second LED array 32 is positioned offset from the first membrane panel 6, and the second LED array 32 is positioned offset from the second membrane panel 7. The first membrane panel 6 and the second membrane panel 7 may be made of a type of material such that the at least one type of material may allow passage of UVL and may be heat resistant. The at least one type of material may include material such as, but is not limited to, synthetic non-cellulosic (for example, polysulfone). Further, the first membrane panel 6 and the second membrane panel 7 may be disposed of in a manner such that each membrane panel may face each other and may be proximal to each other. Further, the facing and the proximity, in an instance, may allow circulating of the quantity of plasma between each membrane panel. Further, in some embodiments, the flow clearance 33 between the first membrane panel 6 and the second membrane panel 7 is based on the circulating of the quantity of plasma may include dimensions, in an instance, of 1 millimeter or less than 1 millimeter. The quantity of plasma is pumped through the flow clearance 33 during Step D. Thus, the quantity of plasma smoothly flows through the bio-compatible channel 5.

Further, the flow clearance 33, in an instance, may allow maximum exposure of the quantity of plasma to UVL. Further, a prime volume of an amount of the quantity of plasma in the primary UVL device 4, in an instance, may be in a range of 100-150 milliliters based on the flow clearance 33. Further, in some embodiments, thickness of each membrane panel may include dimensions, in an instance, of 20 micrometers or microns for allowing the maximum exposure of the one or more blood cells to UVL. Further, in an instance, each membrane may include a thick inner layer in contact with the quantity of plasma and a thicker outer layer with minimal or no porosity. Further, in some embodiments, the surface area of each membrane panel of the bio-compatible channel 5, in an instance, is 450 square centimeters (a surface area of 30 centimeters by 15 centimeters). Further, the surface area, in an instance, may be smaller or larger than 450 square centimeters. Further, the bio-compatible channel 5 may result in an increased surface area such as, for example, the bio-compatible channel 5 may include three membrane panels of 450 square centimeters each may result in the increased surface area of 1350 square centimeters. Further, each membrane panel of the bio-compatible channel 5 may include a flat shape. Further, the flat shape, in an instance, may correspond to a rhomboidal shape such that each membrane panel may minimize turbulence inside the bio-compatible channel 5. Further, in some embodiments, an outside of the bio-compatible channel 5 may be supported by a grid of thin rods. Further, the grid of the thin rods, in an instance, may include at least one type of material such that the at least one type of material may prevent deformation (or external bulging) that may be caused by a positive pressure caused by the input peristaltic pump 1. Further, the at least one type may include material such as, but is not limited to, hard plastic or PVC.

Figure 11:
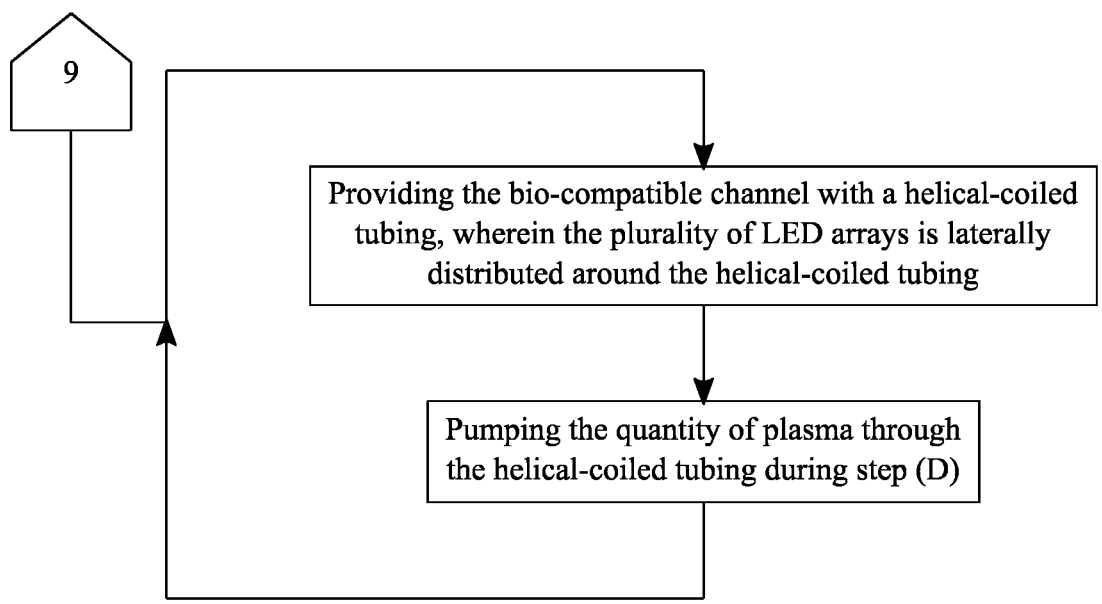
FIG. 11 is a flowchart illustrating the subprocess on how the quantity of plasma flows through the bio-compatible channel.

Alternatively and with reference to FIGS. 5 and 11, in order for the quantity of plasma to smoothly flow through the primary UVL device 4, the following subprocess is executed. The bio-compatible channel 5 is provided with a helical-coiled tubing 8 instead of the first membrane panel 6 and the second membrane panel 7, and the plurality of LED arrays 9 is laterally distributed around the helical-coiled tubing 8. The helical-coiled tubing 8 may include a small cross-section tubing of dimensions, such as, but are not limited to, an internal diameter of 1-2 millimeters, 10-30 micrometers of wall thickness, 1-2 centimeters width, and 1-2 meters length for allowing the maximum exposure to and absorption of UVL (for example, 2 centimeters width×1 millimeter height×200 centimeters length). Further, the first membrane panel 6 and the second membrane panel 7 may offer a lower internal resistance to the flow of the quantity of plasma in comparison to the helical-coiled tubing 8. The quantity of plasma of pumped through the helical-coiled tubing 8 during Step D. Thus, the quantity of plasma smoothly flows through the primary UVL device 4.

Further, in other embodiments, the first membrane panel 6 and the second membrane panel 7 may include a heating component and another UVL source. Further, each membrane panel may be exposed to the other UVL source on each side of each membrane panel. Further, the exposing, in an instance, may increase the exposure of the quantity of plasma to UVL. Further, in a case where the helical-coiled tubing 8 is used instead of the first membrane panel 6 and the second membrane panel 7, the helical-coiled tubing 8 may include a heating component. Further, one or more ultraviolet (UV) lamps may be disposed of in an outside and/or around the helical-coiled tubing 8 and/or inside of the helical-coiled tubing 8.

Figure 2:
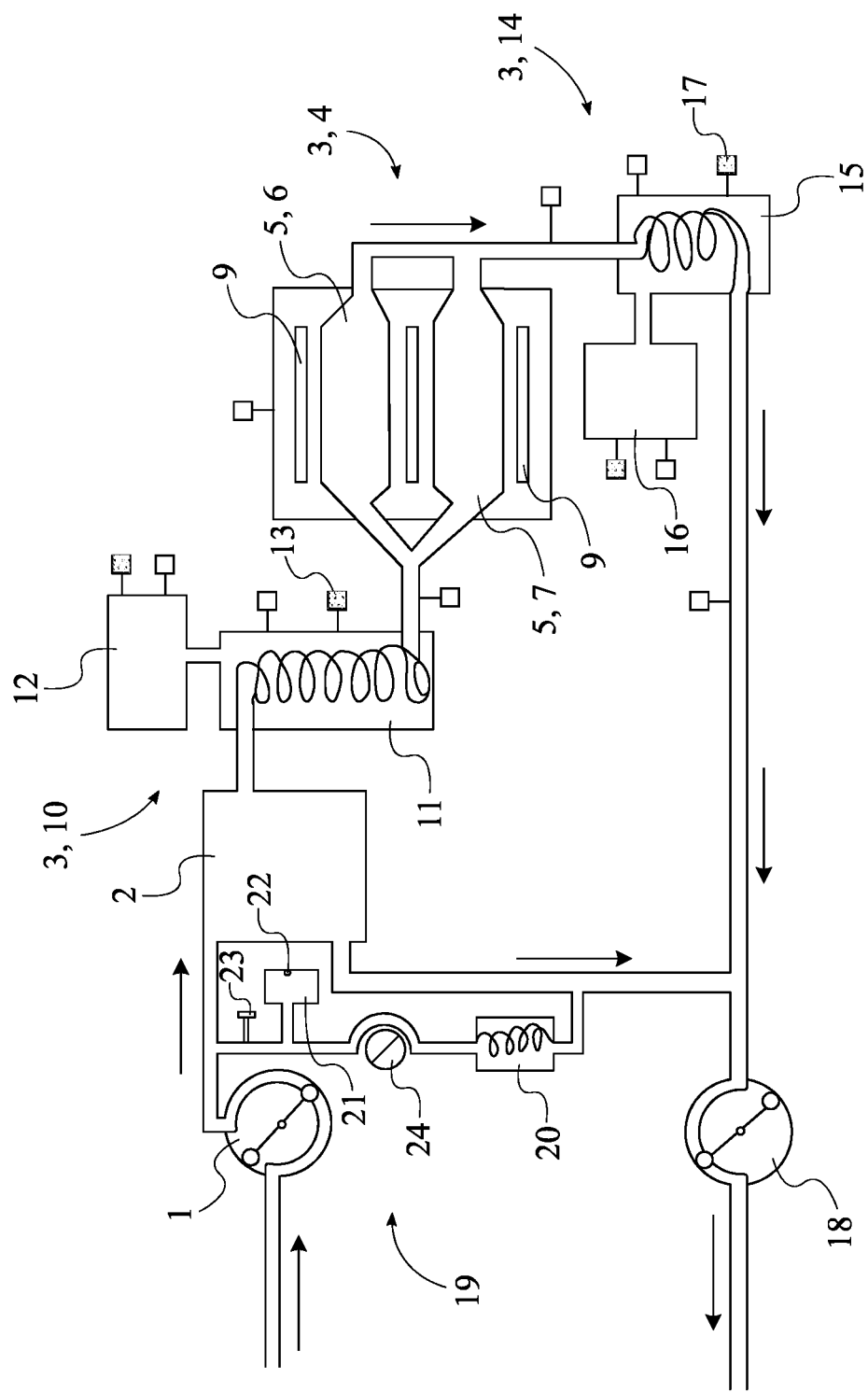
FIG. 2 is a diagram illustrating the system of the present invention with the blood-treating system.
Figure 12:
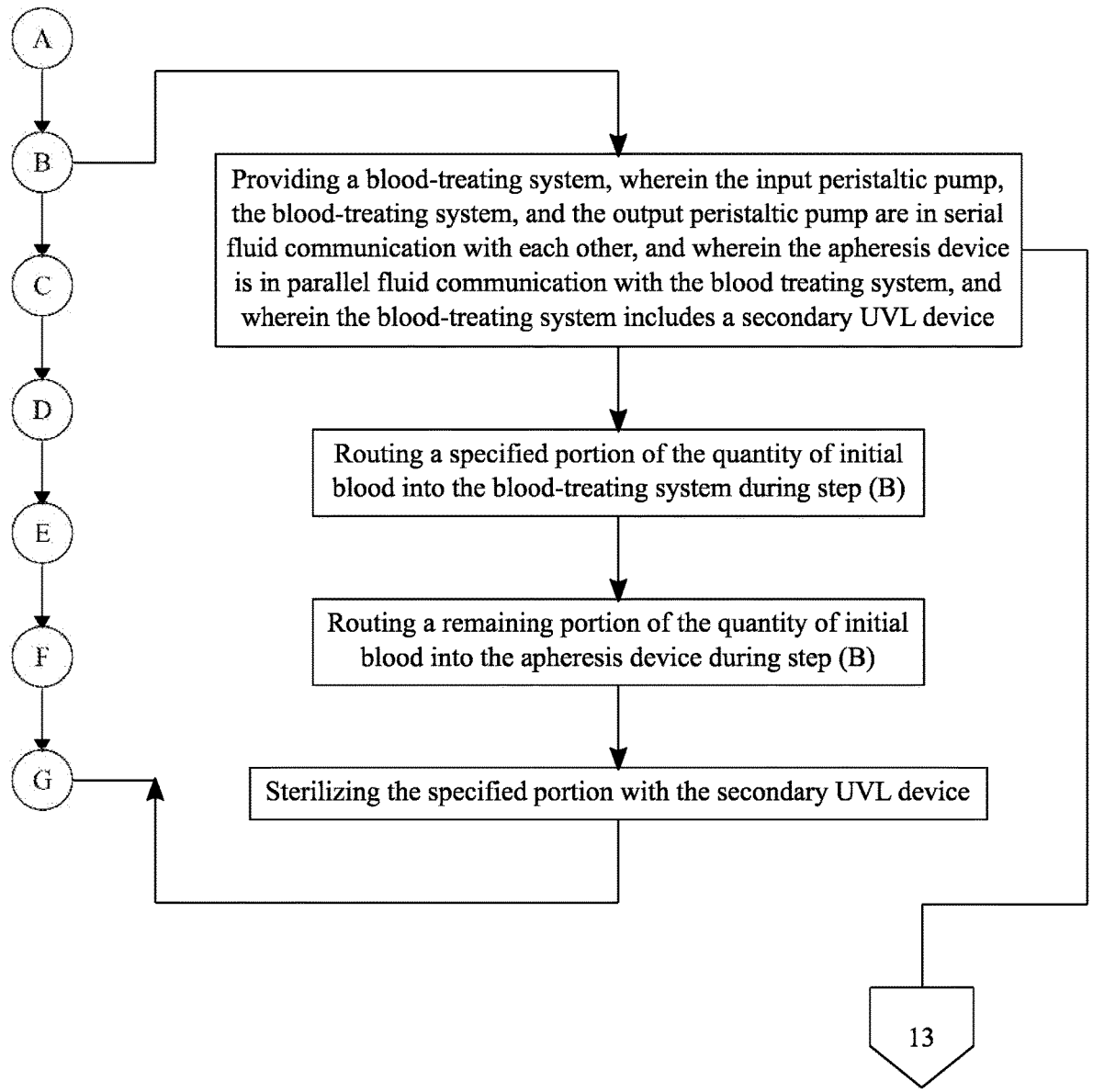
FIG. 12 is a flowchart illustrating the subprocess of using a blood-treating system.

In order for the present invention to additionally treat a quantity of unseparated blood and with reference to FIGS. 2 and 12, the following subprocess is executed. The system includes a blood-treating system 19. The input peristaltic pump 1, the blood-treating system 19, and the output peristaltic pump 18 are in serial fluid communication with each other, the apheresis device 2 is in parallel fluid communication with the blood-treating system 19, and the blood-treating system 19 includes a secondary UVL device 20. The blood-treating system 19 may be located between a needle suctioning the quantity of initial blood from the patient and the apheresis device 2. A specified portion of the quantity of initial blood is routed into the blood-treating system 19. The specified portion is a specific amount from the quantity of initial blood that is safe to be treated. A remaining portion of the quantity of initial blood is routed into the apheresis device 2. The remaining portion is the rest of the quantity of initial blood that is eventually separated. Finally, the secondary UVL device 20 sterilizes the specified portion. The secondary UVL device 20 emits a plurality of shortwaves, and the wavelength of each of the plurality of shortwaves is at least 253 nanometers. Thus, a quantity of unseparated blood is additionally treated by the present invention.

Figure 13:
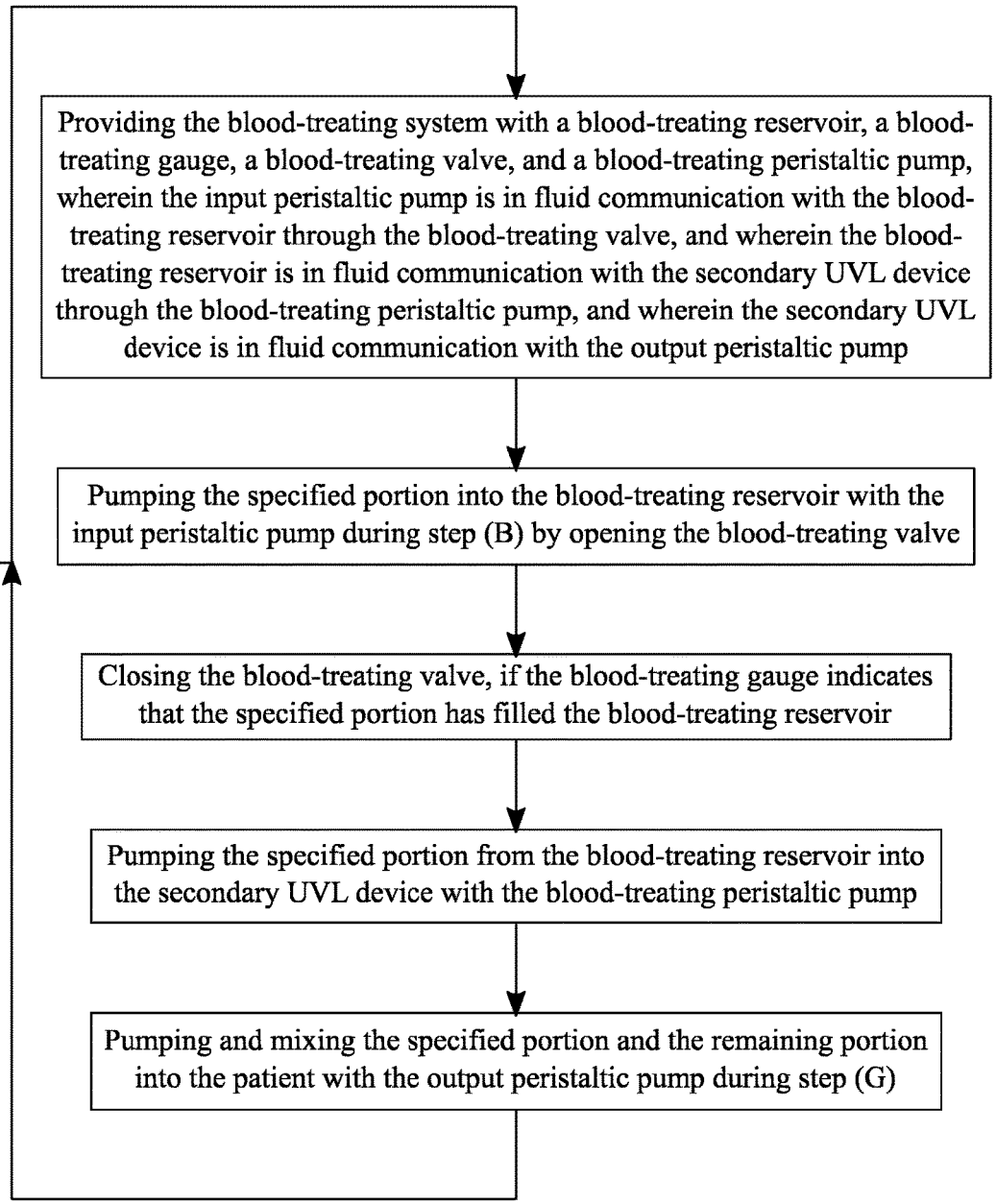
FIG. 13 is a flowchart illustrating the subprocess of how the blood-treating system is used.

Further, in order to return the treated specified portion of the quantity of initial blood to the patient and with reference to FIGS. 2 and 13, the following subprocess is executed. The blood-treating system 19 further includes a blood-treating reservoir 21, a blood-treating gauge 22, and a blood-treating peristaltic pump 24. The input peristaltic pump 1 is in fluid communication with the blood-treating reservoir 21 through the blood-treating valve 23, the blood-treating reservoir 21 is in fluid communication with the secondary UVL device 20 through the blood-treating peristaltic pump 24, and the secondary UVL device 20 is in fluid communication with the output peristaltic pump 18. In more detail, the blood-treating reservoir 21 stores the specified portion, the blood-treating gauge 22 measures the volume of the specified portion stored in the blood-treating reservoir 21, the blood-treating valve 23 allows a desired volume of the specified portion to flow into the blood-treating reservoir 21, and the blood-treating peristaltic pump 24 propels the specified portion towards a secondary UVL device 20. The input peristaltic pump 1 pumps the specified portion into the blood-treating reservoir 21 during Step B by opening the blood-treating valve 23. In more detail, opening the blood-treating valve 23 allows the quantity of initial blood to flow into the blood-treating reservoir 21. The blood-treating peristaltic pump 24 is used to accelerate the flow of the quantity of initial blood. The blood-treating valve 23 is then closed, if the blood-treating gauge 22 indicates that the specified portion has filled the blood-treating reservoir 21. In more detail, the blood-treating valve 23 automatically closes to stop the flow of the quantity of initial blood into the blood-treating reservoir 21 once a safe amount of the quantity of initial blood as filled the blood-treating reservoir 21. The blood-treating peristaltic pump 24 then pumps the specified portion from the blood-treating reservoir 21 into the secondary UVL device 20. In more detail, the specified portion flows into the secondary UVL device 20 in order to be treated. Finally, the output peristaltic pump 18 pumps and mixes the specified portion and the remaining portion into the patient during Step E. Thus, the treated specified portion of the quantity of initial blood is returned to the patient.

Figure 3:
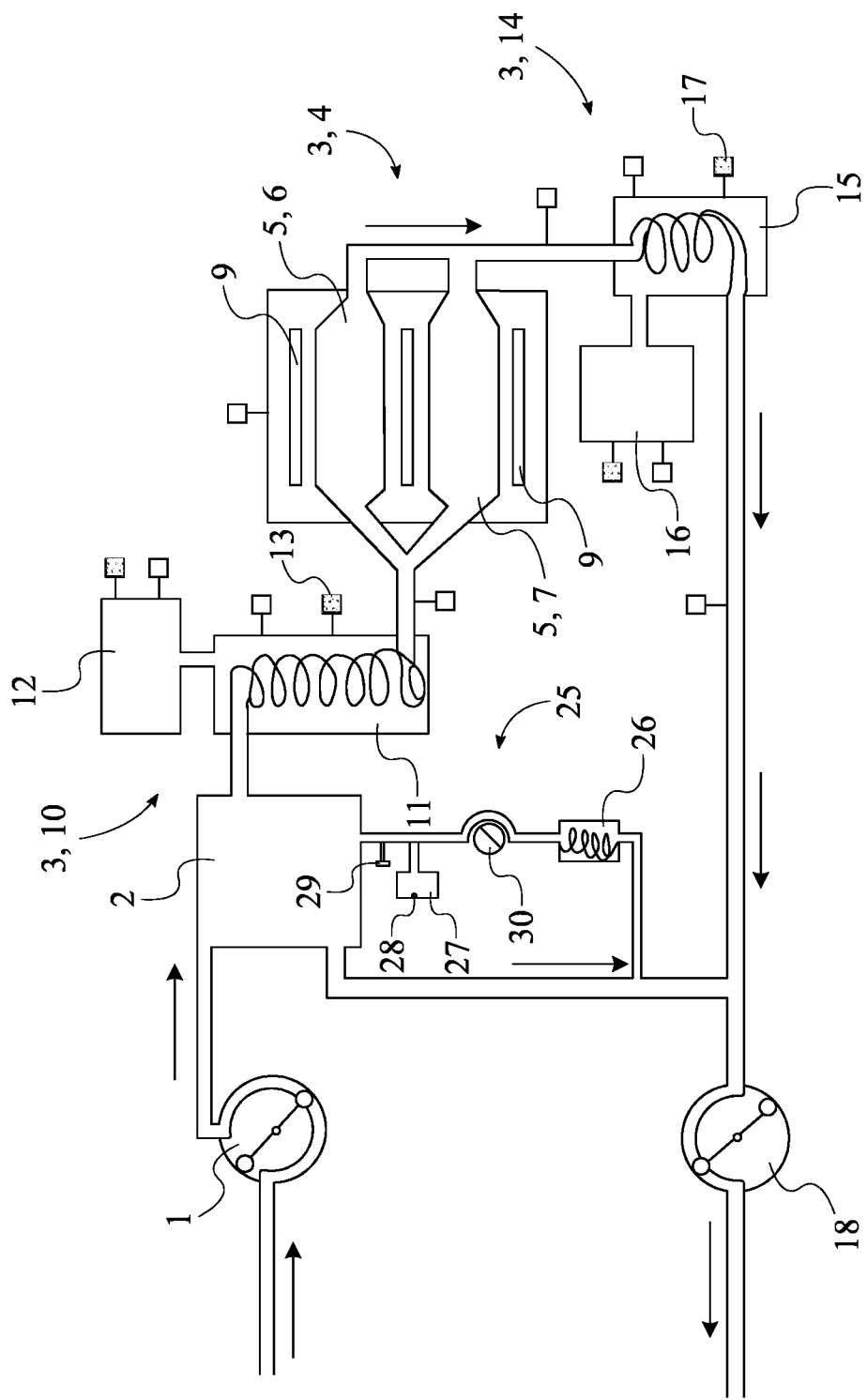
FIG. 3 is a diagram illustrating the system of the present invention with the leucocyte-treating system.
Figure 14:
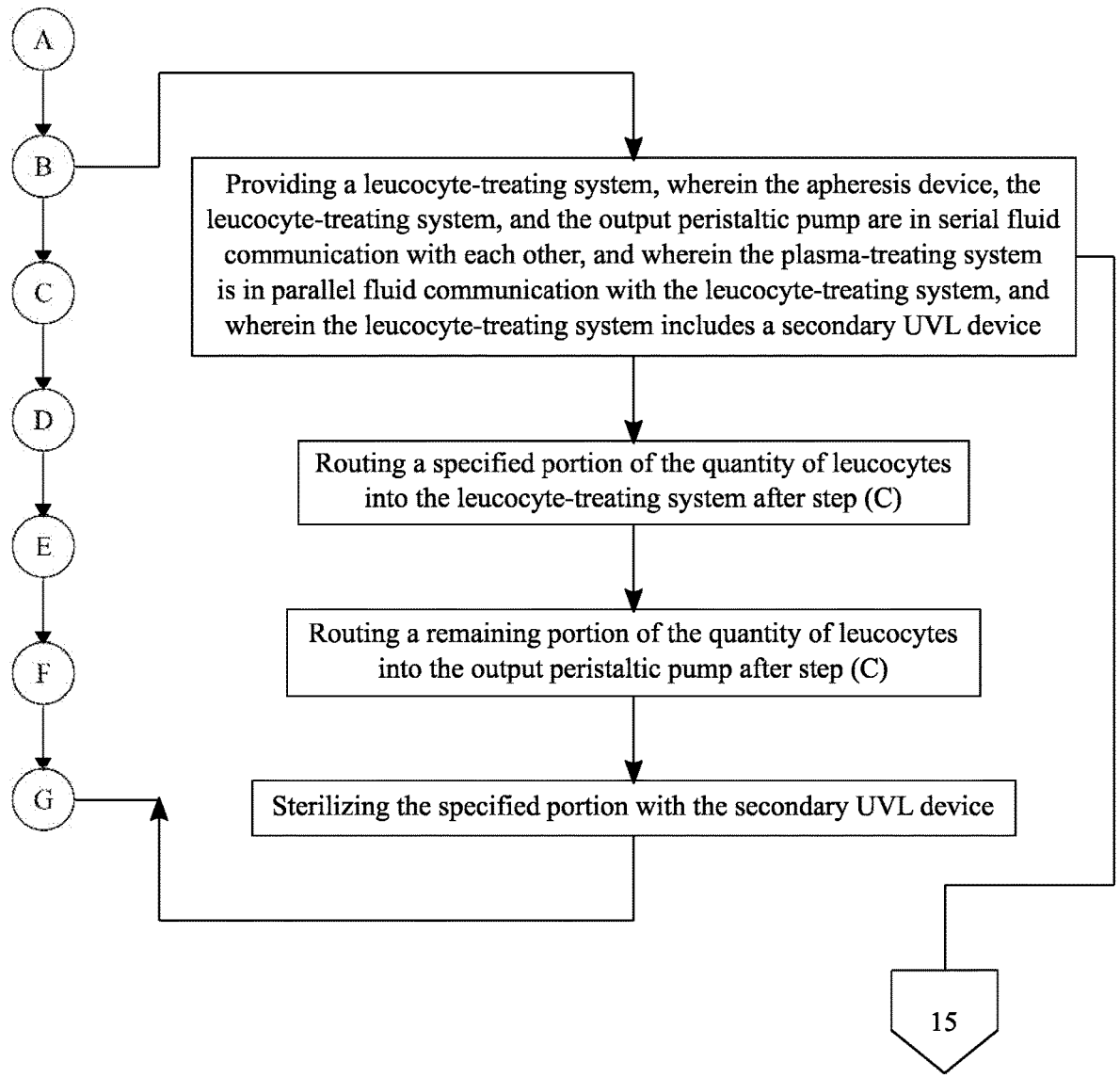
FIG. 14 is a flowchart illustrating the subprocess of using a leucocyte-treating system.

Alternatively, in order for the present invention to additionally treat a quantity of leucocytes and/or a buffy coat and with reference to FIGS. 3 and 14, the following subprocess is executed. The system includes a leucocyte-treating system 25. The apheresis device 2, the leucocyte-treating system 25, and the output peristaltic pump 18 are in serial fluid communication with each other, the plasma-treating system 3 is in parallel fluid communication with the leucocyte-treating system 25, and the leucocyte treating system includes a secondary UVL device 26. The leucocyte-treating system 25 may be positioned adjacent to the apheresis device 2. A specified portion of the quantity of leucocytes is routed into the leucocyte-treating system 25. The specified portion is a specific amount from the quantity of leucocytes that is safe to be treated. A remaining portion of the quantity of leucocytes is routed into the output peristaltic pump 18. The remaining portion is the rest of the quantity of leucocytes that is returned in an untreated state to the patient. Finally, the secondary UVL device 26 sterilizes the specified portion. The secondary UVL device 26 emits a plurality of shortwaves, and the wavelength of each of the plurality of shortwaves is at least 253 nanometers. Thus, a quantity of leucocytes is additionally treated by the present invention.

Figure 15:
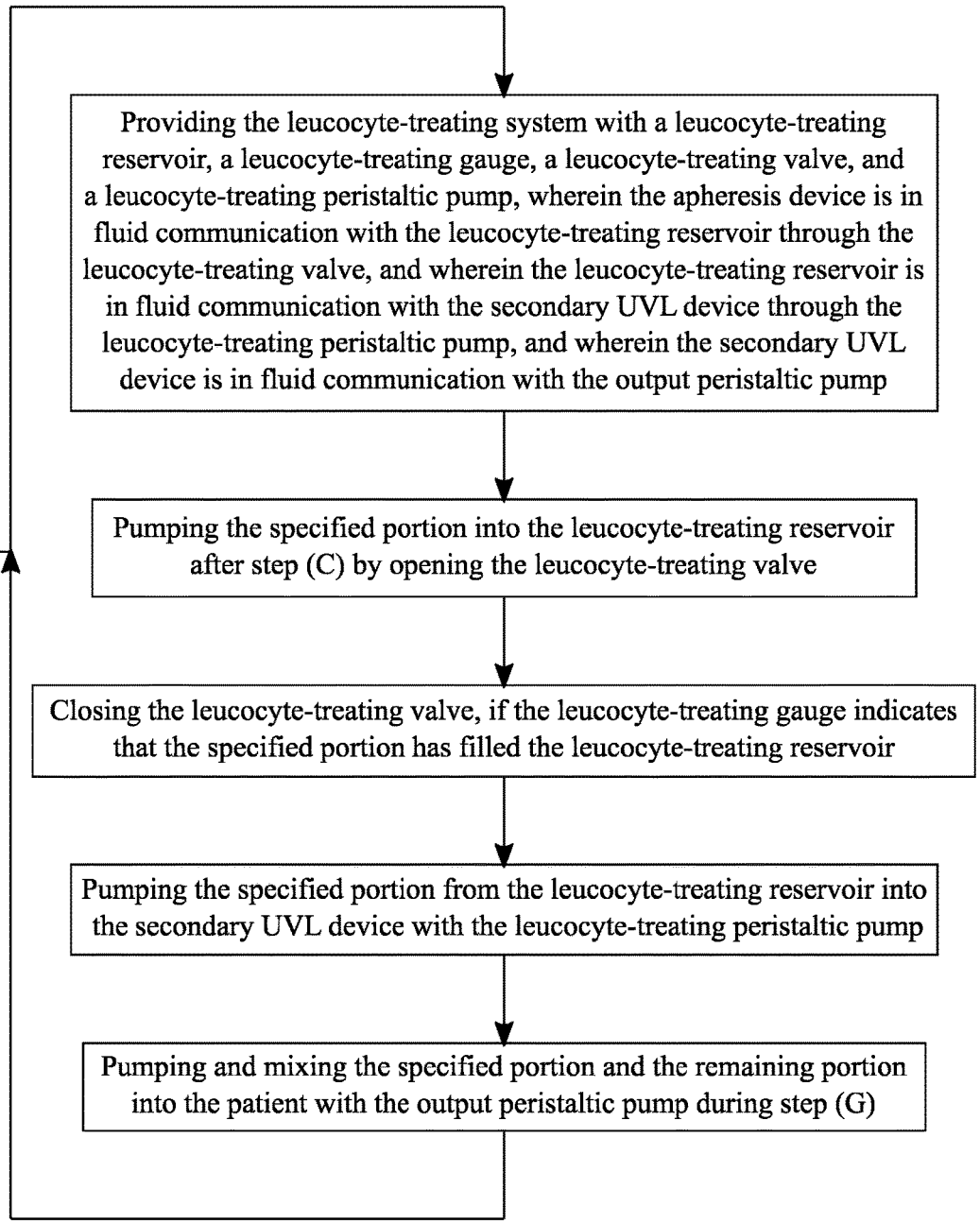
FIG. 15 is a flowchart illustrating the subprocess of how the leucocyte-treating system is used.

Further, in order to return the treated specified portion of the quantity of leucocytes to the patient and with reference to FIGS. 3 and 15, the following subprocess is executed. The leucocyte-treating system 25 further includes a leucocyte-treating reservoir 27, a leucocyte-treating gauge 28, and a leucocyte-treating peristaltic pump 30. The apheresis device 2 is in fluid communication with the leucocyte-treating reservoir 27 through the leucocyte-treating valve 29, the leucocyte-treating reservoir 27 is in fluid communication with the secondary UVL device 20 through the leucocyte-treating peristaltic pump 30, and the secondary UVL device 20 is in fluid communication with the output peristaltic pump 18. In more detail, the leucocyte-treating reservoir 27 stores the specified portion, the leucocyte-treating gauge 28 measures the volume of the specified portion stored in the leucocyte-treating reservoir 27, the leucocyte-treating valve 29 allows a desired volume of the specified portion to flow into the leucocyte-treating reservoir 27, and the leucocyte-treating peristaltic pump 30 propels the specified portion towards a secondary UVL device 20. The specified portion is pumped into the leucocyte-treating reservoir 27 after Step C by opening the leucocyte-treating valve 29. In more detail, opening the leucocyte-treating valve 29 allows the quantity of leucocytes to flow into the leucocyte-treating reservoir 27. The leucocyte-treating peristaltic pump 30 is used to accelerate the flow of the quantity of leucocytes. The leucocyte-treating valve 29 is then closed, if the leucocyte-treating gauge 28 indicates that the specified portion has filled the leucocyte-treating reservoir 27. In more detail, the leucocyte-treating valve 29 automatically closes to stop the flow of the quantity of leucocytes into the leucocyte-treating reservoir 27 once a safe amount of the quantity of leucocytes as filled the leucocyte-treating reservoir 27. The leucocyte-treating peristaltic pump 30 then pumps the specified portion from the leucocyte-treating reservoir 27 into the secondary UVL device 20. In more detail, the specified portion flows into the secondary UVL device 20 in order to be treated. Finally, the output peristaltic pump 18 pumps and mixes the specified portion and the remaining portion into the patient during Step E. Thus, the treated specified portion of the quantity of leucocytes is returned to the patient.

Alternatively, the present invention can also cool the quantity of plasma to 2 to 3 degrees Celsius below normal to induce hypothermia which is a standard treatment for patients with acute brain injury caused by a stroke, brain trauma or post cardiac arrest. In this case, the heating device 10 and the primary UVL device 4 are shut down and only the cooling device 14 is used. This method of cooling the body should be more effective than the methods currently used; applying cold pads to the skin around the neck, axilla and groins do not decrease the core temperature rapidly and the intravascular cooling devices are invasive and can cause serious complications such as thromboembolism and infection.

Supplemental Description

The present disclosure aims to treat infections for which there is no specific treatment available like epidemics or pandemics caused by viruses, i.e. Covid-19 and sepsis caused by antibiotic resistant pathogens, which are a major cause of mortality and cause immense economic loses. Further, the present disclosure describes an apparatus which fulfills a need to treat such infections because it inactivates pathogens in blood and modulate the excessive inflammatory response that usually is present in these patients and is a major cause of mortality. Further, the present disclosure describes ways as to how the apparatus circulates a patient's blood volume, continuously and many times, through an extracorporeal circuit, separates the plasma, red blood cells and leucocytes or buffy coat, exposes the plasma with added riboflavin to high temperature and UVL to inactivate viruses or any other pathogen, cools the treated plasma to normal temperature or induces hypothermia, mixes the plasma with the blood cells, returns the reconstituted blood to the patient, and also separately exposes whole blood, leucocytes or the buffy coat to UVL for a few seconds to modulate the immuno-response.

Further, the present disclosure describes the apparatus which provides the following benefits, such as:
  (a) A therapeutic method available to treat these often-fatal infections may be provided if viremias or bacteremia are present.
  (b) The magnitude of an infection and of the inflammation may decrease, thereby allowing innate immunity to overcome the infection.
  (c) The plasma temperature may decrease to normal before returning the blood to the patient.
  (d) The morbidity and mortality of the patients undergoing the treatment may decrease.
  (e) Hypothermia in patients with acute brain damage caused by strokes or after cardiac arrest may be induced.

Further, the present disclosure aims to treat blood plasma with heat and UVL with added riboflavin. Further, the present describes the apparatus that may inactivate pathogens in plasma with added riboflavin as a photosensitizer by circulating the plasma at a slow flow rate over several hours through a heat chamber to increase the plasma temperature to a maximum of 60° C. and through a chamber of UVL of 280-360 nm wavelengths, as a result of which susceptibility of the pathogens to inactivation by UVL increases which allows achieving same results than a higher dose of UVL without damaging plasma proteins. Further, the heat may inactivate viruses by denaturing the secondary structures of proteins and altering the proteins involved in attachment and replication within a host cell (R29) and its effect depends on the temperature level and duration of exposure. Further, the heat is currently being used to inactivate pathogens in plasma such as in pasteurization (60° C. for up to 10 hrs) (R30-R36), dry heat of up to 100° C. for 30 min, 80° C. for 72 hours (R37-R38) or 60° C. for 10-30 minutes (R29). Based on the above studies, it is assumed that heating the plasma up to 60° C. increases the inactivation of pathogens by UVL at least 50%.

Similarly, the continuous spectrum of UVL has germicidal effects by causing irreparable damage to the DNA and RNA of viruses and other pathogens (R39-R41). Ultraviolet C (UVC) and Ultraviolet B (UVB) radiations (280-320 nm) cause pyrimidine dimers (R29) and with or without enhancers such as methylene blue, riboflavin or amotosalen to sensitize pathogens (R42-R49) rapidly deactivate viruses, bacteria and parasites, and both are currently used to sterilize whole blood, plasma and platelets concentrate (R50-R61).

Further, high doses of UVL of 280-365 nm for 5,10, and 15 minutes, damages plasma proteins and coagulation factors, and exposure to UVL of 253 nm (R62) for 6, 12, and 25 minutes damages coagulation and complement proteins, kininogen, thrombin, albumin serum amyloid P component, CRP, retinol binding protein and causes oxidative stress but it occurs at low stoichiometry and this effect appeared to be modest.

When riboflavin is exposed to UVL, it oxidizes nucleic acids (DNA or RNA) through electron transfer reactions, resulting in the inhibition of the pathogen genome and inactivation. Since riboflavin is a vitamin and its photo-products are non-toxic, there is no need for their removal from the body. It can be administered intravenously at a dose of 10-80 mg/Kg per day in divided doses, the first one given before the treatment.

The effectiveness of UVL to inactivate pathogens in plasma depends on the dose delivered and the number of pathogens in plasma such as:
(a) The dose of UVL delivered depends on:
  The intensity of the light, which in turn depends on the source of light and the distance from the source. Narrow wave lengths of UVL, i.e., UVL C of 253 nm have higher penetration and carries higher energy than broad wave lengths i.e., UVL A of 405 nm. The intensity is inversely proportional to the distance between the source and each pathogen circulating inside the UVL chamber and also depends on the tube's wall transmission of light.
  The time of exposure of each unit of a pathogen to UVL during an entire treatment depends on the transit time during one pass through the UVL chamber and the number of times the same pathogen circulates through the chamber and both of them depend on the duration of the treatment and the plasma flow rate. The transit time during one pass also depends on the length of the circuit inside the UVL chamber.
  The transit time is brief, around 10-12 seconds and the plasma flow rate are 50 mL/min but it could be higher. However, during the many passes through the chamber during a several hours long treatment, each pathogen would have accumulated a total exposure of around 2-4 minutes which is assumed would be equivalent to the 6 minutes that a bag of plasma (and the pathogens in it) is exposed to UVL and riboflavin when the plasma is sterilized before transfusion. This would be the case because:
  i. Inside the apparatus disclosed, the plasma circulates through the UVL chamber as a thin layer and most of the pathogens are in close contact with the UVL source all the time whereas in the plasma for transfusion even if it is constantly stirred to generate turbulence, the proximity to the UVL source of each pathogen is intermittent, only when moved closer to the bag's wall by the turbulence, and likely occurs for a few seconds during the six minutes of exposure.
  ii. Previous studies have demonstrated that short time exposure inactivates pathogens (R6), that a significant decrease of pathogen count occurs within 2 minutes of exposure to UVL of 320-400 nm without enhancer (R63), and after one minute of exposure to UVL of 254 nm (R64). Other studies have demonstrated that increasing the time of exposure to UVL of 280-360 nm from 2 minutes to 4 minutes increases the inactivation of viruses by 266% and from 4 min to 6 mins by 122% and adding riboflavin to UVL exposure increases the virus inactivation by 50%-90% (R63) and adding Psoralen to UVL increases inactivation of SARS-Covid 100-fold (R29).
  iii. Heat and UVL with added riboflavin to the plasma are expected to increase the inactivation of pathogens by at least 150% above UVL alone, so it is assumed that an exposure of 2 minutes to heat, UVL and riboflavin would be equivalent to a 4-5 minutes exposure to UVL alone (10 seconds per pass×12 passes during 8 hours treatment).
  iv. Even if minimal structural alterations to a pathogen are made and not total inactivation by heat/ UVL+riboflavin, this could impair the ability of viruses to attach to and enter cells and replicate or alter the functions of other pathogens. Even though longer exposures could be more effective this could cause excessive damage to plasma proteins and coagulations factors (R18,R62,R63, R65). Plasma and not whole blood is exposed to UVL because of the damage it causes to leucocytes DNA and RNA.
The plasma flow rate also contributes to determine the transit time during one pass and the number of passes during one treatment. For example, if a patient's blood volume is 4 L and the plasma is 50% of the blood volume or 2 L, at a blood flow rate of 100 ml/min through the apheresis component and a plasma flow rate of 50 ml/min; during an 8 hours treatment, 24 L of plasma circulates through the device and the 2 L of plasma and each pathogen in the plasma circulates 12 times through the apparatus and is exposed to UVL and heat.
A higher plasma flow rate would decrease the time of exposure to heat and UVL during each pass through the chambers but will increase the number of times the entire volume of plasma will circulate through the chambers. As in the above example, at a plasma flow rate of 50 ml/min during an 8 hrs. treatment, the plasma circulates 12 times through the circuit but at a plasma flow rate of 100 mL/min it would circulate 24 times but at a shorter transit time during each pass.

(b) The effectiveness of UVL also depends on the number of pathogens present in plasma and this depends on the replication rate, the reproductive cycle of pathogens (principally viruses) and the phase of the infection.

The burst size of viruses, that is, the number of virions formed in one cell in a day, ranges between 100000 (poliovirus) to a few thousand (poxvirus). Some viruses, i.e. HIV 1 releases more particles to plasma than others, i.e. HIV2 and influenza.

The extreme pathogenicity of H5N1 is directly linked to the ability of the virus to replicate rapidly, and swiftly attain high steady-state titers in the lungs within 48 hours after infection (R66).

The reproductive cycle of pathogens. This varies between 8 hrs for picornavirus or more than 72 hours for some herpesviruses. HIV-1 doubling time is around 15 hours and Epstein Barr is 42 hours.

The phase of the infection; during the maturation and release phase of viral infections the reproduction is higher than during early and late phases (eclipse and decay phase) (R67).

Thus, a high burst size, short reproducible cycle and the maturation and release phase, in the case of viral infections, are associated with a higher viral load in plasma.

Further, the present disclosure aims to treat whole blood with UVL. Further, UVL applied to whole blood was successfully used to treat sepsis in dogs and humans in 1928 (R90) and later in 1934 (R91) and 1947 (R92). However, its use was discarded and forgotten by the introduction of penicillin, vaccines and other antibiotics (R93). On these occasions, 3.5 mL/Kg of whole blood or 5-7% of the blood volume was exposed to UVL 253 nm, extra corporeally and for 10 seconds.

Further, it is known that UVL applied to leucocytes could have immune-stimulatory or immune-suppressive effects depending on the dose. At low dose it causes apoptosis of leucocytes, especially of T cells (R94-R95) which are the most sensitive (R18), increases the secretion of immune suppressive cytokines (IL-4,IL-10) from macrophages and neutrophils (R96), decreases the production of pro-inflammatory cytokines, i.e., IL-12 by monocytes and of IL-2, IL-4, IL-5, TNF-α and IFN-γ (R18), increases complement activation (R97, R18), degrades DNA in white cells (which usually self-repaired if the energy delivered is less than 16 J/cm2 (R39, R18), increases phagocytic activity of macrophages and granulocytes and causes oxidative stress in neutrophils (R18), and peroxidation of lipids in cell membranes and of LDL and HCL in plasma. UVL equally affects CD4 (helper) and CD8 (suppressor) cells. A low dose of UVL, i.e., 0.5-1.0 mJ/cm2 is sufficient to kill most T cells and T cells and cytokines reduction is dose dependent (R18).

High doses of UVL also decreases production of oxidants by polymorphonuclear cells, effect that can be inhibited by alpha-tocopherol. If the dose is higher than 16 J/cm2 it causes more disruption of Ca2 cellular membrane channel and increased intracellular Ca2 in T cells more than non-T cells which cause cell death. High doses also decrease the ability of cellular DNA to self-repair (R18) and inhibit the immunologic response mediated by white blood cells as effectively as gamma irradiation (R98-R99).

Furthermore, broadband UVA of 320-400 nm and narrowband of 231 nm are routinely used for photopheresis (extracorporeal exposure of circulating leucocytes, principally T cells to UVL) to treat Cutaneous T Cell Lymphoma (CTCL) and Graft Versus Host Disease (GVHD) (R100-R101) and other skin diseases. However, the treatment of CTCL and GVHD usually takes at least 15 min 2-3 times per week, not 10 seconds.

The treatment of leucocytes in a small volume of blood (whole blood) or a small volume of leucocytes probably is beneficial in sepsis because UVL damages mononuclear cells, principally T cells, and other leucocytes and decreases pro-inflammatory cytokines levels, increases anti-inflammatory cytokines levels which should decrease an excessive inflammatory response and cytokine storm.

However, there may be other mechanisms in play to explain why treating a small number of mononuclear cells (principally T cells) and other leucocytes producing cytokines would have such a significant benefit in patients with sepsis.

Further, the present disclosure aims to treat plasma by cooling it to a normal temperature before it is returned to the patient should be beneficial when the plasma temperature is raised by heat and UVL or fever caused by infections. Further, fever is caused by inflammatory cytokines released from immune cells and even though it may be advantageous to patients, (R102-R104), a high temperature can have detrimental effects (R105); a body temp of 43° C. can cause structural cells damage (R106), hyperthermia, i.e. heat stroke, 41° C./105.80 F, causes thrombocytopenia, elevation of D-Dimers and myoglobin in plasma (R107) and once core temperature reaches 104 F (40° C.) cellular damage occurs initiating a cascade of events that may lead to organ failure and death. With high fever or hyperpyrexia, there is a systemic inflammatory response, increased cell wall permeability, and a cascade of events that include tissue hypoxia, metabolic acidosis and severe organ dysfunction (R108-R112). High fever also can have possible noxious effects in patients with cerebral damage, neuropsychiatric disorders or limited cardiorespiratory reserve and observations studies have reported associations between the magnitude of fever and patient's mortality (R113).

Further, the apparatus disclosed could also cool the plasma to 2° C.–3° C. below normal to induce hypothermia which is a standard treatment for patients with acute brain injury caused by a stroke, brain trauma, or post cardiac arrest. This method of cooling the body should be more effective than the methods currently used; applying cold pads to the skin around the neck, axilla and groins do not decrease the core temperature rapidly and the intravascular cooling devices are invasive and can cause serious complications such as thromboembolism and infection (R114-R115). Further, the present disclosure aims to provide benefit with the help of the apparatus disclosed, such as:

(a) It will be the only therapeutic method available to treat often fatal acute infections for which there is no treatment available if viremia or bacteremia are present.

(b) The inactivation of pathogens in plasma will decrease the severity of the acute infections.

(c) Decreasing the severity of an infection will decrease the magnitude of the inflammatory response and this should decrease the magnitude of organs failure and the patients' morbidity and mortality.

(d) Decreasing the severity of infection and inflammation should also benefit in the immunosuppressive phase of sepsis during which reactivation of common viruses such as EBV, CMV, HSV, HHV-6, polyoma virus and the anellovirus TTV is common (R116). However, the procedure may not provide benefits in patients with infections without viremia or bacteremia or in chronic infections even if viremia is present, i.e., human immunodeficiency virus or hepatitis C.

(e) The treatment of whole blood with UVL will modulate the immuno-response. In the early phase of sepsis, will decrease the immuno-response by increasing the release of anti-inflammatory cytokines and decreases the release of pro-inflammatory cytokine and in the late or immunosuppressive phase by decreasing the magnitude of immunosuppression.

(f) The heparin used to prevent clotting of the blood inside the apheresis component of the circuit would contribute to treat the coagulation disorder often found in many patients with Covid-19 infection (R117) or sepsis (R118).

(g) If used to induce hypothermia in patients with acute brain damage it will contribute to decrease morbidity and mortality.

(h) The power supply could be provided by a battery, allowing its use in remote areas.

Further, the procedure associated with the apparatus disclosed has some challenges, such as:

1. It does not eradicate the pathogens from the entire body nor from inside cells.
2. It is impossible to know the pathogen load of the entire body, the percentage of the load that is circulating in the plasma and to estimate the impact that inactivating pathogens in plasma has on the severity of an infection and inflammation, especially in viral infections, in which most of the viruses are located and multiply inside cells and not in the plasma.

However, even though each intracellular viral particle replicates exponentially inside a cell, an immense number of newly formed particles are constantly released to the plasma after replication. Since each of the particles that enter the plasma will eventually lodge into other cells throughout the body where they will also exponentially replicate and continuously release newly formed particles to the plasma, inactivating particles in the plasma at any given time should contribute to exponentially decrease the total body and plasma viral or other pathogens load.

For this reasons, it would be more beneficial to provide a longer treatment because they inactivate pathogens already present in the plasma and many of the newly released to the plasma, in particular if the virus has a slow replication rates, whereas viruses with fast replication rate like SARS-Covid-2 and H5N1 would equally benefit of shorter treatments, starting treatments in the early or acute phases of infections because of the higher pathogens plasma levels, and daily or continuously given treatments for a few days.

That the inactivation of viruses or other pathogens present in the plasma should decrease the severity of an infection and of an inflammation, is supported by the following observations:

(a) Covid-19 RNAaemia (viremia) has been exclusively found in critically ill patients and appeared to reflect the illness severity. Likewise, the level of IL-6 in plasma was 10 times higher in these critically ill patients than in other covid-19 infected patients, and the level of RNAaemia and of IL-6 correlated with the severity of vital signs changes (R68). Also, a correlation between Covid-19 titers and clinical findings (R69) and lung injury (R70).

(b) A correlation has also been found between viral load (in plasma) and the severity of Dengue (R71-R73), enterovirus (R74), Epstein Bar Virus (R75), Cytomegalic Virus (R76), Hepatitis E (R77), Hepatitis A (R78), Rhinovirus (R79), in lower respiratory tract infection in children (R80), Respiratory Syncytial virus in infants (R81), Hantavirus and lung injury (R82), and varicella (R83), and the severity and response to treatment of hepatitis C (R84-R86), and HIV (R87), infections.

(c) A correlation between bacteria load and severity of infection in neonates (R88), and between the severity of infection and mortality in adults has been reported (R89).

Further, one or more thermostats may be disposed of in the at least one heating component (23), in the reservoir of the at least one heating component (24), in the at least one cooling component (25) and in the reservoir of the at least one cooling component (26). Further, one or more sensors of temperature and/or flow rate may be disposed of along a length of the at least one circuit of tubes.

Further, in some embodiments, a precise length, wall thickness, an internal diameter and shape of the one or more tubes carrying the blood plasma, the one or more blood cells or the whole blood, the thickness and surface area of each membrane, the flow rate of the blood plasma, the one or more UVL sources, and a most effective and safe wavelength of UVL for the blood plasma (for example, in a range of 280-360 nm) and for the whole blood (for example, 253 nm or broader wavelength), a maximal temperature and a time of exposure to heat and to UVL, and duration of treatment may be determined experimentally.

Further, the apparatus for facilitating extracorporeal sterilization and cooling of the blood products, in an instance, may include a system configured for performing one or more tasks related to the apparatus for facilitating extracorporeal sterilization and cooling of the blood products. Further, the system may include a communication device, a processing device, and a storage device. Further, the one or more tasks may include, but are not limited to, activating one or more peristaltic pumps, activating at least one component of one or more components of the apparatus, and so on. Further, the tasks may be performed based on an interaction of a user with at least one device associated with a user. Further, the interaction, in an instance, may be based on an application programming interface (API) platform associated with the apparatus for facilitating extracorporeal sterilization and cooling of the blood products. Further, the user, in an instance, may download an application on the at least one device associated with the user. Further, the at least one device may be any IoT based device, such as a smartphone, a smartwatch, a laptop, a desktop, etc.

Further, the communication device may be configured to establish a communication link with the at least one device. Further, the communication device may be configured to receive a signal based on the interaction from the at least one device over the communication link. Further, the processing device may be configured to process the signal based on the receiving. Further, the storage device may be configured to store one or more predefined conditions associated with the waterproof apparatus for the bicyclist based on the interaction with the at least one device. Further, the processing device may be configured to determine the one or more predefined conditions based on the processing. Further, the processing device may be configured to generate one or more steps related to the one or more predefined conditions. Further, the one or more tasks may be performed based on the one or more steps.

Further, the activation of the one or more peristaltic pumps may be based on the interaction of the user with the at least one device. Further, the interaction may include, but is not limited, tapping, swiping, etc. Further, a condition for the activation of the one or more peristaltic pumps may be predefined based on the storing. Further, the API may allow the user to select one or more options for the activation of the one or more peristaltic pumps based on the interaction.

Further, the activation of the at least one component of one or more components of the apparatus may be based on the interaction of the user with the at least one device. Further, the interaction may include, but is not limited to, the tapping, the swiping, etc. Further, a condition of the activation of the at least one component of one or more components of the apparatus may be predefined based on the storing. Further, the API may allow the user to select one or more options for the activation of the at least one component of one or more components of the apparatus based on the interaction.

Further, the apparatus disclosed may be used to treat systemic infections caused by a virus or other pathogens for which there is no effective treatment available if viremia or bacteremia are present or suspected and there is a severity of illness, measured as a Sequential Organ Failure Assessment (SOFA) score of 3-4 or higher or an increase of >2 in the score or a SOFA respiratory score of >1 (Pa02/FI02<400 mmHg). Also, a quick SOFA (qSOFA) with a score of >2 or higher and an elevated lactate (>2 mmols) and procalcitonin levels could be used.

Further, the method may include a step of drawing, heparinized blood from a vein of the patient. Further, heparin (or any other anticoagulant) may be used to prevent coagulation of the blood and separated blood cells during transit. Further, the heparin may be administered as a bolus or infusion. Further, the heparinized blood may circulate through at least one apheresis component at a flow rate of 100 mL/min. Further, blood plasma is separated from one or more blood cells (such as, red cells and leucocytes) and may be circulated at a flow rate of 50 mL/min subsequent to the circulating through the at least one apheresis component, through at least one heating component, at least one UVL component (360-390 nm) and at least one cooling component. Further, the blood plasma may be mixed with the one or more blood cells (such as, separated red blood cells and leucocytes) and may be returned to the patient through the vein.

Further, the method may include a step of exposing, a whole blood (in an instance, may be 3.5 mL/Kg or 200-250 mL of the whole blood) or leucocytes and/or a buffy coat (in an instance, may be 5-10 mL of the leucocytes and/or the buffy coat) to UVL of 253 nm wavelength for at least 10 seconds, subsequent to the treatment of the blood plasma. Further, treated whole blood based on the exposing may be mixed with treated plasma and the one or more blood cells (such as, separated red blood cells), and may be returned to the patient through the vein. Further, a treatment of the one or more blood cells, in an instance, may be performed subsequent to the treatment of the blood plasma in an instance of low level of the riboflavin.

Further, the blood plasma may be treated for at least 6-8 hours daily or continuously for at least 2-3 days in early phases of infection. Further, the treatment of the blood plasma may continue in an instance where a significant improvement in the patient may be present or may be stopped in an instance where no improvement and/or worsening of Sequential Organ Failure Assessment (SOFA) score is noticed. Further, the treatment of the whole blood or the leucocytes may be repeated in at least 24-72 hours, as the one or more blood cells may be irradiated to die subsequent to assessing of clinical response and one or more changes in a severity of the infection. Further, one or more markers may be measured to assess changes in the immunologic response which may include changes such as, but are not limited to, in T cells count (CD4 and CD8), cytokines levels, etc.

Although the invention has been explained in relation to its preferred embodiment, it is to be understood that many other possible modifications and variations can be made without departing from the spirit and scope of the invention as hereinafter claimed.

What is claimed is:

1. A method for facilitating the extracorporeal inactivation of pathogens of blood products, the method comprising the steps of:
   (A) providing an input peristaltic pump, at least one apheresis device, at least one plasma-treating system, and an output peristaltic pump, wherein the input peristaltic pump, the apheresis device, the plasma-treating system, and the output peristaltic pump are in fluid communication with each other, and wherein the plasma-treating system includes at least one primary ultraviolet light (UVL) device, at least one heating device, and at least one cooling device;
   (B) pumping a quantity of initial blood out of a patient into the apheresis device with the input peristaltic pump;
   (C) separating the quantity of initial blood into a quantity of plasma, a quantity of leucocytes, and a quantity of red blood cells with the apheresis device;
   (D) heating the quantity of plasma to a first specified temperature with the heating device;
   (E) irradiating the quantity of plasma with the primary UVL device;
   (F) cooling the quantity of plasma to a second specified temperature with the cooling device;
   (G) pumping and mixing the quantity of plasma, the quantity of leucocytes, and the quantity of red blood cells as a quantity of treated blood into the patient with the output peristaltic pump;
   providing a blood-treating system, wherein the input peristaltic pump, the blood-treating system, and the output peristaltic pump are in serial fluid communication with each other, and wherein the apheresis device is in parallel fluid communication with the blood treating system, and wherein the blood-treating system includes a secondary UVL device;
   routing a specified portion of the quantity of initial blood into the blood-treating system during step (B);
   routing a remaining portion of the quantity of initial blood into the apheresis device during step (B); and
   sterilizing the specified portion with the secondary UVL device.

2. The method as claimed in claim 1, wherein the first specified temperature is a maximum of 140 degrees Fahrenheit.

3. The method as claimed in claim 1, the method comprising the steps of:
   providing the heating device with a helical-coiled heat exchanger, a heating element, and a thermostat, wherein the apheresis device, the helical-coiled heat exchanger, and the primary UVL device are in serial fluid communication with each other, and wherein the heating element is in conductive thermal communication with the helical-coiled heat exchanger;
   setting the first specified temperature with the thermostat; and
   heating the quantity of plasma to the first specified temperature with the heating element as the quantity of plasma flows through the helical-coiled heat exchanger.

4. The method as claimed in claim 1, wherein the second specified temperature is a maximum of 98 degrees Fahrenheit.

5. The method as claimed in claim 1, the method comprising the steps of:
providing the cooling device with a helical-coiled heat exchanger, a cooling element, and a thermostat, wherein the primary UVL device, the helical-coiled heat exchanger, and the output peristaltic pump are in serial fluid communication with each other, and wherein the cooling element is in conductive thermal communication with the helical-coiled heat exchanger;
setting the second specified temperature with the thermostat; and
cooling the quantity of plasma to the second specified temperature with the cooling element as the quantity of plasma flows through the helical-coiled heat exchanger.

6. The method as claimed in claim 1, wherein the primary UVL device emits a plurality of shortwaves, and wherein the wavelength of each of the plurality of shortwaves ranges from 280 nanometers to 360 nanometers.

7. The method as claimed in claim 1, the method comprising the steps of:
providing the primary UVL device with at least one bio-compatible channel and a plurality of light emitting diodes (LED) arrays, wherein the heating device, the bio-compatible channel, and the cooling device are in serial fluid communication with each other, and wherein the plurality of LED arrays is in optical communication with the bio-compatible channel; and
irradiating the quantity of plasma with the plurality of LED arrays as the quantity of plasma flows through the bio-compatible channel during step (D).

8. The method as claimed in claim 7, the method comprising the steps of:
providing the bio-compatible channel with a first membrane panel and a second membrane panel, wherein the first membrane panel is positioned parallel and offset to the second membrane panel by a flow clearance, and wherein the plurality of LED arrays includes at least one first LED array and at least one second LED array, and wherein the first LED array is positioned offset from the first membrane panel, and wherein the second LED array is positioned offset from the second membrane panel; and
pumping the quantity of plasma through the flow clearance during step (D).

9. The method as claimed in claim 7, the method comprising the steps of:
providing the bio-compatible channel with a helical-coiled tubing, wherein the plurality of LED arrays is laterally distributed around the helical-coiled tubing; and
pumping the quantity of plasma through the helical-coiled tubing during step (D).

10. The method as claimed in claim 1, the method comprising the steps of:
providing the blood-treating system with a blood-treating reservoir, a blood-treating gauge, a blood-treating valve, and a blood-treating peristaltic pump, wherein the input peristaltic pump is in fluid communication with the blood-treating reservoir through the blood-treating valve, and wherein the blood-treating reservoir is in fluid communication with the secondary UVL device through the blood-treating peristaltic pump, and wherein the secondary UVL device is in fluid communication with the output peristaltic pump;
pumping the specified portion into the blood-treating reservoir with the input peristaltic pump during step (B) by opening the blood-treating valve;
closing the blood-treating valve, if the blood-treating gauge indicates that the specified portion has filled the blood-treating reservoir;
pumping the specified portion from the blood-treating reservoir into the secondary UVL device with the blood-treating peristaltic pump; and
pumping and mixing the specified portion and the remaining portion into the patient with the output peristaltic pump during step (G).

11. The method as claimed in claim 1, wherein the secondary UVL device emits a plurality of shortwaves, and wherein the wavelength of each of the plurality of shortwaves is at least 253 nanometers.

12. A method or facilitating the extracorporeal inactivation of pathogens of blood products, the method comprising the steps of:
(A) providing an input peristaltic pump, at least one apheresis device, at least one plasma-treating system, and an output peristaltic pump, wherein the input peristaltic pump, the apheresis device, the plasma-treating system, and the output peristaltic pump are in fluid communication with each other, and wherein the plasma-treating system includes at least one primary ultraviolet light (UVL) device, at least one heating device, and at least one cooling device;
(B) pumping a quantity of initial blood out of a patient into the apheresis device with the input peristaltic pump;
(C) separating the quantity of initial blood into a quantity of plasma, a quantity of leucocytes, and a quantity of red blood cells with the apheresis device;
(D) heating the quantity of plasma to a first specified temperature with the heating device;
(E) irradiating the quantity of plasma with the primary UVL device;
(F) cooling the quantity of plasma to a second specified temperature with the cooling device;
(G) pumping and mixing the quantity of plasma, the quantity of leucocytes, and the quantity of red blood cells as a quantity of treated blood into the patient with the output peristaltic pump;
providing a leucocyte-treating system, wherein the apheresis device, the leucocyte-treating system, and the output peristaltic pump are in serial fluid communication with each other, and wherein the plasma-treating system is in parallel fluid communication with the leucocyte-treating system, and wherein the leucocyte-treating system includes a secondary UVL device;
routing a specified portion of the quantity of leucocytes into the leucocyte-treating system after step (C);
routing a remaining portion of the quantity of leucocytes into the output peristaltic pump after step (C); and
sterilizing the specified portion with the secondary UVL device.

13. The method as claimed in claim 12, the method comprising the steps of:
providing the leucocyte-treating system with a leucocyte-treating reservoir, a leucocyte-treating gauge, a leucocyte-treating valve, and a leucocyte-treating peristaltic pump, wherein the apheresis device is in fluid communication with the leucocyte-treating reservoir through the leucocyte-treating valve, and wherein the leucocyte-treating reservoir is in fluid communication with the secondary UVL device through the leucocyte-treating peristaltic pump, and wherein the secondary UVL device is in fluid communication with the output peristaltic pump;

pumping the specified portion into the leucocyte-treating reservoir after step (C) by opening the leucocyte-treating valve;

closing the leucocyte-treating valve, if the leucocyte-treating gauge indicates that the specified portion has filled the leucocyte-treating reservoir;

pumping the specified portion from the leucocyte-treating reservoir into the secondary UVL device with the leucocyte-treating peristaltic pump; and pumping and mixing the specified portion and the remaining portion into the patient with the output peristaltic pump during step (G).

14. The method as claimed in claim 12, wherein the secondary UVL device emits a plurality of shortwaves, and wherein the wavelength of each of the plurality of shortwaves is at least 253 nanometers.

* * * * *